(12) United States Patent
Zorn et al.

(10) Patent No.: US 8,617,842 B2
(45) Date of Patent: Dec. 31, 2013

(54) ENZYMES FOR USE IN ENZYMATIC BLEACHING OF FOOD PRODUCTS

(75) Inventors: Holger Zorn, Dortmund (DE); Manuela Scheibner, Hannover (DE); Bärbel Hulsdau, Hannover (DE); Ralf Günter Berger, Hannover (DE); Lex De Boer, Wateringen (NL); Roelf Bernhard Meima, Kamerik (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/067,476

(22) Filed: Jun. 3, 2011

(65) Prior Publication Data
US 2011/0262974 A1 Oct. 27, 2011

Related U.S. Application Data

(62) Division of application No. 11/988,365, filed as application No. PCT/EP2006/064132 on Jul. 12, 2006, now Pat. No. 7,981,636.

(30) Foreign Application Priority Data

Jul. 12, 2005 (WO) .................. PCT/EP2005/053329
Dec. 15, 2005 (WO) .................. PCT/EP2005/056825

(51) Int. Cl.
*C12P 21/06* (2006.01)

(52) U.S. Cl.
USPC ........ 435/69.1; 435/7.1; 435/320.1; 435/252; 530/350; 530/300

(58) Field of Classification Search
None
See application file for complete search history.

(56) References Cited

U.S. PATENT DOCUMENTS

| | | | |
|---|---|---|---|
| 7,041,486 B1 | 5/2006 | Syoda et al. | ................. 435/192 |
| 2006/0127533 A1 | 6/2006 | Roos et al. | |
| 2006/0154842 A1 | 7/2006 | Sugio et al. | |

FOREIGN PATENT DOCUMENTS

| | | |
|---|---|---|
| EP | 1 156 106 | 11/2001 |
| WO | 02/086114 | 10/2002 |
| WO | 2005/004616 | 1/2005 |
| WO | 2005/067735 | 7/2005 |

OTHER PUBLICATIONS

International Search Report for PCT/EP2006/064132 mailed Oct. 12, 2006, four pages.
Gelinas et al. "Oxido-reductases and lipases as dough-bleaching agents" Cereal Chemistry, vol. 75, No. 6, pp. 810-814 (Nov. 1998).
Grosch et al. "Formation of volatile carbonyl compounds and cooxidation of β-carotene by lipoxygenase from wheat, potato, flax, and beans" Journal of Agriculture and Food Chemistry, vol. 24, No. 3, pp. 456-459 (1976).
Johjima et al. "Isolation and cDNA cloning of novel hydrogen peroxide-dependent phenol oxidase from the basidiomycete *Termitomyces albuminosus*" Applied Microbiology Biotechnology, vol. 61, No. 3, pp. 220-225 (Feb. 2003).
Kiefer et al. "Identification and characterization of a mammalian enzyme catalyzing the asymmetric oxidative cleavage of provitamin A" Journal of Biological Chemistry, vol. 276, No. 17, pp. 14110-14116 (Apr. 2000).
Von Lintig et al. "Filling the gap in vitamin A research: Molecular identification of an enzyme cleaving β-carotene to retinal" vol. 275, No. 16, pp. 11915-11920 (Apr. 2000).
Zorn et al. "A peroxidase from *Lepista irina* cleaves β, β-carotene to flavor compounds" Biological Chemistry, vol. 384, No. 7, pp. 1049-1056 (Jul. 2003).
Zorn et al. "Cleavage of β, β-carotene to flavor compounds by fungi" Applied Microbiology and Biotechnology, vol. 62, No. 4, pp. 331-336 (Sep. 2003).

*Primary Examiner* — Hope Robinson
(74) *Attorney, Agent, or Firm* — Nixon & Vanderhye

(57) ABSTRACT

The present invention relates to novel polypeptides according to caroase 01-05 or any functional equivalents of any of them, suitable for use in a method for preparing a food products having increased whiteness, the use of the enzyme to increase whiteness of at least part of a food product, a process for preparing a food product wherein the enzyme is used and the food product obtained.

3 Claims, No Drawings

ENZYMES FOR USE IN ENZYMATIC BLEACHING OF FOOD PRODUCTS

This application is a divisional of application Ser. No. 11/988,365, filed 8 Feb. 2008, U.S. Pat. No. 7,981,636, which is a 371 of PCT/EP2006/064132 filed 12 Jul. 2006 which designated the U.S. and claims priority to PCT Application No. PCT/EP2005/053329 filed 12 Jul. 2005, and PCT Application No. PCT/EP2005/056825 filed 12 Dec. 2005, the entire contents of each of which are hereby incorporated by reference.

The present invention relates to novel enzymes suitable for use in a method for preparing a food products having increased whiteness, the use of the enzyme to increase whiteness of at least part of a food product, a process for preparing a food product wherein the enzyme is used and the food product obtained.

In some types of food product a white colour of at least part of the food product is seen as desirable, for example in dairy products, for example cheeses, whey, butter, and milk powder and in flour-based products, for example bread and noodles.

The raw materials or intermediate products of such food products however may comprise pigments, which can cause off-white to yellow colour of the food product. Examples of such pigments are carotenoids (carotenes and xanthophylls) and flavones.

In white bread for example, a white crumb is seen as a desirable property. A whiter crumb may be obtained by using enzymes such as catalase, peroxidase, lipase and/or lipoxygenase, see for instance 'Oxido-reductases and Lipases as Dough-Bleaching Agent' by P. Gélines et al, Cereal Chem, 75(6), 810-814 (1998). All enzymes mentioned have a bleaching effect on the crumb. At present, the baking industry mostly uses enzyme active soy flour, which contains lipoxygenases. The lipoxygenases in the soy flour are capable of bleaching wheat flour pigments as a result of the action of free radicals and other reactive oxygen species that are formed during the oxidation of fatty acids by lipoxygenase. This reaction is called a co-oxidation. In soy flour, three lipoxygenases are present, L1, L2 and L3 whereby L2 and L3 possess the best bleaching activity (W. Grosch, G. Laskawy and F. Weber, J. Agric. Food Chem 24 (1976), 456). Soy flour not only contains lipoxygenases but also the fatty acids that are necessary for the bleaching effect, resulting in an improved bleaching effect.

A disadvantage associated with the use of soybeans as a source of lipoxygenase, is the fact that nowadays most of the soybeans are genetically modified (GMO). Since there is a worldwide consumer preference for using non-GMO derived bread improving additives, an alternative for the soy lipoxygenases is highly required. The known enzymes other than the lipoxygenases L2 and L3 from soy have the disadvantage that their performance is not as good as the lipoxygenases from soy. In practice, to obtain the desired whiteness, these enzymes are to be combined with cofactors or other enzymes to reach the desired level of whiteness of the crumb. Peroxidases catalyze non-enzymatically the oxidation, by molecular oxygen, of unsaturated compounds e.g. unsaturated fatty acids. (C. E. Eriksson et. al. JAOS 48 (1971) 442). These oxidized fatty acids generate radicals that probably react with flour pigments to less coloured products in a similar way as the lipoxygenase reaction products.

It is the object of the present invention to provide novel enzymes suitable for preparing a food product having increased whiteness of at least part of the food product.

Surprisingly was found that the bleaching enzymes according to the invention are capable of directly converting pigment into a form that results in increased whiteness. These enzymes can in various ways exert their direct bleaching effect on the pigments. For example, they can directly convert the pigments by saturating unsaturated bonds in the pigments via for example hydrogenation, or they can directly cleave the pigments, forming degradation products. With the term direct is meant that these enzymes act upon the pigment as substrate itself. Use of co-factors for reaching the conversion is not specifically excluded.

Furthermore it was found that the bleaching polypeptide according to the invention is capable of directly cleaving pigments (a so-called cleaving enzyme). Suitable cleaving enzymes according to the invention are enzymes that are capable of cleaving carotenoids (carotenes and xanthophylls) and flavones. Carotenoids can be cleaved in two different ways, central and eccentric. Central cleavage of carotenoids results in formation of retinoids ($C_{20}$-compounds). Eccentric cleavage can yield a more diverse group of compounds, as for example abscisic acid. An enzyme capable of central cleavage of carotenoids is for example β-carotene 15,15'-monooxygenase (EC 1.14.99.36) as described in for example EP-A-1031623 and J. Lintig and K Vogt (2000) J. Biol. Chem. 275, 11915. This enzyme was formerly known as beta-carotene 15,15'-dioxygenase=EC 1.13.11.21.

An additional advantage of the use of enzymes capable of central cleavage is the formation of retinoids. These are essential components in vision. β-carotene is cleaved into two molecules of retinal. This retinal can be modified to retinol, also known as vitamin A. Examples of enzymes capable of eccentric cleavage of carotenoids are 9-cis-epoxycarotenoid dioxygenase (e.g. X. Qin and J. A. D. Zeevaart (1999), Proc. Nat. Acad. Science, 96, 15354) and β-carotene 9', 10'-dioxygenase (e.g. Kiefer et al. (2001), J. Biol. Chem. 287, 14110).

This object is reached by the novel enzyme as disclosed in the present invention.

In a first aspect, the invention relates to isolated polypeptides having bleaching activity and one or more characteristics selected from the group consisting of:
1) An isolated polypeptide according to any one of SEQ ID NO: 08-12 or functional equivalents of any of them;
2) An isolated polypeptide obtainable by expressing a polynucleotide according to any one of SEQ ID NO: 01-07 or functional equivalents of any of them or a vector comprising said polynucleotides or functional equivalents of any of them in an appropriate host cell, e.g. *Aspergillus niger*, and
3) A polypeptide comprising at least one of SEQ ID NO: 13-17.

The term 'polypeptides having bleaching activity' is here and hereafter defined as a polypeptide that is capable of beta-carotene degradation or a polypeptide that is capable of bleaching food products. Beta-carotene degradation can be measured for example by at least one of the methods as disclosed in the Materials and Method section of this patent application, for example the method according to Zorn or the method according to Aziz. Preferably, the polypeptide according to the invention shows bleaching activity in both the Aziz and the Zorn assay. The capability of bleaching food products can be determined by comparing the whiteness of a product A, wherein the investigated polypeptide is used in its preparation, to the whiteness of a product B, that only differs from product A in the sense that the investigated polypeptide was not used in its product, for example visually or by known reflection measurements, whereby the b-factor of a product A will be closer to 0 than the b-factor of a product B, in case the investigated polypeptide has bleaching activity.

Even more preferably, the polypeptide according to the invention is capable of beta-carotene degradation as determined according to Zorn and which is capable of bleaching food products as determined by measurement of the b-factor by reflection measurement. Most preferably, the polypeptide according to the invention is capable of beta-carotene degradation as determined according to Zorn, in case the food products that are bleached have an irregular surface structure, eg. crumb of bread, since then the reflection measurement method is not that reliable.

In a preferred embodiment, the invention provides a purified polypeptide is provided. The polypeptides according to the invention include the polypeptides encoded by the polynucleotides according to the invention. Especially preferred is a polypeptide according to SEQ ID NO: 08-12 or functional equivalents of any of them.

Fusion proteins comprising a polypeptide according to the invention are also within the scope of the invention. The invention also provides methods of making the polypeptides according to the invention.

For the avoidance of doubt; SEQ ID NO: 01-07 refers to the group of DNA sequences containing SEQ ID NO: 01, SEQ ID NO: 02, SEQ ID NO: 03, SEQ ID NO: 04, SEQ ID NO: 05, SEQ ID NO: 06, and SEQ ID NO: 07; SEQ ID NO: 08-12 refers to the group of protein sequences containing SEQ ID NO: 08, SEQ ID NO: 09, SEQ ID NO: 10, SEQ ID NO: 11 and SEQ ID NO: 12; and SEQ ID NO: 13-18 refers to the group of protein sequences containing SEQ ID NO: 13, SEQ ID NO: 14, SEQ ID NO: 15, SEQ ID NO: 16 and SEQ ID NO: 17. Furthermore, the terms caroase-01, caroase-02, caroase-03, caroase-04, caroase-05 (the whole group referred to as 'caroase-01-05') are used for polypeptides having respectively SEQ ID NO: 08-12.

In a second aspect, the invention provides for polynucleotides having a nucleotide sequence that hybridises preferably under highly stringent conditions to a sequence according to any one of SEQ ID NO: 01-07. Consequently, the invention provides nucleic acids that are about 55%, preferably 65%, more preferably 70%, even more preferably 75%, 80%, 85%, 90%, 95%, 96%, 97%, 98% or 99% homologous to the sequences according to SEQ ID NO: 01-07.

In a more preferred embodiment the invention provides for such an isolated polynucleotide obtainable from fungi, preferably filamentous fungi, in particular *Marasmius* is preferred, for example *M. scorodonius*.

In one embodiment, the invention provides for an isolated polynucleotide comprising a nucleic acid sequence encoding a polypeptide with an amino acid sequence as shown in SEQ ID NO: 08-12 or functional equivalents of any of them.

In a further preferred embodiment, the invention provides an isolated polynucleotide encoding at least one functional domain of a polypeptide according to SEQ ID NO: 08-12 or functional equivalents of any of them.

In a preferred embodiment the invention provides a bleaching enzyme gene according to SEQ ID NO: 01-07. In another preferred embodiment, the invention provides a polynucleotide encoding a bleaching enzyme whose amino acid sequence is shown in SEQ ID NO: 08-12 or variants or fragments of any of those polypeptide.

In a further preferred embodiment, the invention provides for a polynucleotide comprising the coding sequence coding for the polypeptides according to the invention, preferred is the polynucleotide sequence of SEQ ID NO: 01-07.

In a third aspect, the invention also relates to vectors comprising a polynucleotide sequence according to the invention and primers, probes and fragments that may be used to amplify or detect the DNA according to the invention.

In a preferred embodiment, a vector is provided wherein the polynucleotide sequence according to the invention is functionally linked with regulatory sequences suitable for expression of the encoded amino acid sequence in a suitable host cell, such as a bacterium or a filamentous fungus, preferably *Marasmius* for example *M. scorodonius*, *Aspergillus*, for example *A. niger* or *A. oryzae*. The invention also provides methods for preparing polynucleotides and vectors according to the invention.

In a fourth aspect, the invention also relates to recombinantly produced host cells that contain heterologous or homologous polynucleotides according to the invention.

In another embodiment, the invention provides recombinant host cells wherein the expression of a peroxidase according to the invention is significantly increased or wherein the activity of the peroxidase is increased.

In another embodiment the invention provides for a recombinantly produced host cell that contains heterologous or homologous DNA according to the invention and wherein the cell is capable of producing a functional peroxidase according to the invention, preferably a cell capable of over-expressing the peroxidase according to the invention, for example an *Aspergillus* strain comprising an increased copy number of a gene according to the invention.

In a fifth aspect, the invention also relates to the use of the bleaching polypeptide according to the invention in any industrial process, preferably as described herein.

Polypeptides According to the Invention

The invention provides an isolated polypeptide having the amino acid sequence according to any one of SEQ ID NO: 08-12, as well as an amino acid sequence obtainable by expressing the polynucleotide of SEQ ID NO: 01-07 in an appropriate host. Also, a peptide or polypeptide comprising a functional equivalent of the above polypeptides is comprised within the present invention. The above polypeptides are collectively comprised in the term "polypeptides according to the invention"

The terms "peptide" and "oligopeptide" are here and hereafter considered synonymous (as is commonly recognized) and each term can be used interchangeably as the context requires to indicate a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (*Molecular Cloning: A Laboratory Manual*, $2^{nd}$, ed. Cold Spring Harbor Laboratory, Cold Spring Harbor Laboratory Press, Cold Spring Harbor, N.Y., 1989)

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The caroase-01-05 bleaching enzymes according to the invention, or functional equivalents thereof, can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Functional Equivalents

The terms "functional equivalents" and "functional variants" are used interchangeably herein. Functional equivalents of caroase 01-05 DNA are isolated DNA fragments that encode a polypeptide that exhibits at least the same or a better bleaching activity of at least one of the caroase 01-05 *Marasmius scorodonius* bleaching enzyme as defined herein. A functional equivalent of a caroase 01-05 polypeptide according to the invention is a polypeptide that exhibits at least the same or a better bleaching activity of at least one of the caroase 01-05 *Marasmius scorodonius* bleaching enzymes as defined herein.

Functional protein or polypeptide equivalents may contain only conservative substitutions of one or more amino acids of any one of SEQ ID NO: 08-12 or substitutions, insertions or deletions of non-essential amino acids of any of these. Accordingly, a non-essential amino acid is a residue that can be altered in any one of SEQ ID NO: 08-12 without substantially altering the biological function. For example, amino acid residues that are conserved among the caroase-01-05 proteins of the present invention, are predicted to be particularly unamenable to alteration. Furthermore, amino acids conserved among the caroase 01-05 proteins according to the present invention and other peroxidases are not likely to be amenable to alteration.

The term "conservative substitution" is intended to mean that a substitution in which the amino acid residue is replaced with an amino acid residue having a similar side chain. These families are known in the art and include amino acids with basic side chains (e.g., lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine).

Functional nucleic acid equivalents may typically contain silent mutations or mutations that do not alter the biological function of encoded polypeptide. Accordingly, the invention provides nucleic acid molecules encoding caroase 01-05 proteins that contain changes in amino acid residues that are not essential for a particular biological activity. Such caroase 01-05 proteins differ in amino acid sequence from any one of SEQ ID NO: 08-12 yet retain at least one biological activity. In one embodiment the isolated nucleic acid molecule comprises a nucleotide sequence encoding a protein, wherein the protein comprises a substantially homologous amino acid sequence of at least about 55%, 65%, 70%, 75%, 80%, 85%, 90%, 95%, 96%, 97%, 98%, 99% or more homologous to the amino acid sequence shown in any one of SEQ ID NO: 08-12.

For example, guidance concerning how to make phenotypically silent amino acid substitutions is provided in Bowie, J. U. et al., Science 247:1306-1310 (1990) wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, supra, and the references cited therein.

An isolated nucleic acid molecule encoding an caroase 01-05 protein homologous to the protein according to any one of SEQ ID NO: 08-12 can be created by introducing one or more nucleotide substitutions, additions or deletions into the coding nucleotide sequences according to SEQ ID NO: 01-07 such that one or more amino acid substitutions, deletions or insertions are introduced into the encoded protein. Such mutations may be introduced by standard techniques, such as site-directed mutagenesis and PCR-mediated mutagenesis.

The term "functional equivalents" also encompasses orthologues of the *M. scorodonius* caroase 01-05 protein. Orthologues of the *M. scorodonius* caroase 01-05 protein are proteins that can be isolated from other strains or species and possess a similar or identical biological activity. Such orthologues can readily be identified as comprising an amino acid sequence that is substantially homologous to any one of SEQ ID NO: 08-12.

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 55%, preferably 65%, more preferably 70%, even more preferably 75%, 80%, 85%, 90%, 95%, 96%, 97%, 98% or 99% identity or more are defined herein as sufficiently identical.

Also, nucleic acids encoding other caroase 01-05 family members, which thus have a nucleotide sequence that differs from SEQ ID NO: 01-07, are within the scope of the invention. Moreover, nucleic acids encoding caroase 01-05 proteins from different species which thus have a nucleotide sequence which differs from SEQ ID NO: 01-07 are within the scope of the invention.

Nucleic acid molecules corresponding to variants (e.g. natural allelic variants) and homologues of the caroase 01-05 DNA of the invention can be isolated based on their homology to the caroase 01-05 nucleic acids disclosed herein using the DNA disclosed herein or a suitable fragment thereof, as a hybridisation probe according to standard hybridisation techniques preferably under highly stringent hybridisation conditions.

In addition to naturally occurring allelic variants of the caroase 01-05 sequence, the skilled person will recognise that changes can be introduced by mutation into the nucleotide sequences of SEQ ID NO: 01-07 thereby leading to changes in the amino acid sequence of the caroase 01-05 protein without substantially altering the function of the caroase 01-05 protein.

In another aspect of the invention, improved caroase 01-05 proteins are provided. Improved caroase 01-05 proteins are proteins wherein at least one biological activity is improved. Such proteins may be obtained by randomly introducing mutations along all or part of the caroase 01-05 coding sequence, such as by saturation mutagenesis, and the resulting mutants can be expressed recombinantly and screened for biological activity. For instance, the art provides for standard assays for measuring the enzymatic activity of peroxidases and thus improved proteins may easily be selected.

In a preferred embodiment the caroase 01-05 protein has an amino acid sequence according to any one of SEQ ID NO: 08-12 respectively. In another embodiment, the caroase 01-05 polypeptide is substantially homologous to the amino acid sequence according to SEQ ID NO: 08-12 respectively and retains at least one biological activity of a polypeptide according to SEQ ID NO: 08-12 respectively, yet differs in amino acid sequence due to natural variation or mutagenesis as described above.

In a further preferred embodiment, the caroase 01-05 protein has an amino acid sequence encoded by an isolated nucleic acid fragment capable of hybridising to a nucleic acid according to SEQ ID NO: 01-07, preferably under highly stringent hybridisation conditions.

Accordingly, the caroase 01-05 protein is a protein which comprises an amino acid sequence at least about 55%, 65%, 70%, 75%, 80%, 85%, 90%, 95%, 96%, 97%, 98%, 99% or more homologous to the amino acid sequence shown in any one of SEQ ID NO: 08-12 and retains at least one functional activity of the polypeptide according to any one of SEQ ID NO: 08-12.

In another aspect of the invention the polypeptide comprises at least one of the sequences shown in SEQ ID NO: 13-17. Preferably, the polypeptide according to the invention comprises at least two of the sequences shown in SEQ ID NO: 13-17. Most preferably, the polypeptide comprises all of the sequences shown in SEQ ID NO: 13-17.

Functional equivalents of a protein according to the invention can also be identified e.g. by screening combinatorial libraries of mutants, e.g. truncation mutants, of the protein of the invention for peroxidase activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3):327-331).

In addition to the caroase 01-05 gene sequences shown in SEQ ID NO: 01 or 02 for caroase-01; SEQ ID NO: 03 or 04 for caroase-02; SEQ ID NO: 05 for caroase-03; SEQ ID NO: 06 for caroase-04 and SEQ ID NO: 07 for caroase-05 respectively, it will be apparent for the person skilled in the art that DNA sequence polymorphisms that may lead to changes in the amino acid sequence of the caroase-proteins may exist within a given population. Such genetic polymorphisms may exist in cells from different populations or within a population due to natural allelic variation. Allelic variants may also include functional equivalents.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides, can be used as hybridization probes or polymerase chain reaction (PCR) primers. Uses of the nucleic acid molecules of the present invention that do not encode a polypeptide having a caroase 01-05 activity include, inter alia, (1) isolating the gene encoding the caroase 01-05 proteins, or allelic variants thereof from a cDNA library e.g. from other organisms than *M. scorodonius*; (2) in situ hybridization (e.g. FISH) to metaphase chromosomal spreads to provide precise chromosomal location of the caroase 01-05 genes as described in Verma et al., Human Chromosomes: a Manual of Basic Techniques, Pergamon Press, New York (1988); (3) Northern blot analysis for detecting expression of caroase 01-05 mRNA in specific tissues and/or cells and 4) probes and primers that can be used as a diagnostic tool to analyse the presence of a nucleic acid hybridisable to the caroase 01-05 probe in a given biological (e.g. tissue) sample.

Also encompassed by the invention is a method of obtaining a functional equivalent of a caroase 01-05 gene. Such a method entails obtaining a labelled probe that includes an isolated nucleic acid which encodes all or a portion of the sequence according to any one of SEQ ID NO: 08-12 or a variant of any of them; screening a nucleic acid fragment library with the labelled probe under conditions that allow hybridisation of the probe to nucleic acid fragments in the library, thereby forming nucleic acid duplexes, and preparing a full-length gene sequence from the nucleic acid fragments in any labelled duplex to obtain a gene related to the caroase 01-05 gene.

In one embodiment, a caroase 01-05 nucleic acid of the invention is at least 55%, 65%, 70%, 75%, 80%, 85%, 90%, 91%, 92%, 93%, 94%, 95%, 96%, 97%, 98%, 99%, or more homologous to a nucleic acid sequence shown in SEQ ID NO: 01 or 02 for caroase-01; SEQ ID NO: 03 or 04 for caroase-02; SEQ ID NO: 05 for caroase-03; SEQ ID NO: 06 for caroase-04 and SEQ ID NO: 07 for caroase-05 respectively or the complement any of them.

In another preferred embodiment a caroase 01-05 polypeptide of the invention is at least 55%, 65%, 70%, 75%, 80%, 85%, 90%, 91%, 92%, 93%, 94%, 95%, 96%, 97%, 98%, 99%, or more homologous to the amino acid sequence shown in any one of SEQ ID NO: 08-12 respectively.

Polynucleotides

The present invention provides polynucleotides encoding a bleaching enzyme (peroxidase), tentatively called caroase 01-05, having an amino acid sequence according to SEQ ID NO: 08-12 or functional equivalents of any of them. The sequence of the gene encoding caroase 01-05 was determined by amplified cDNA obtained from *Marasmius scorodonius*. The sequence having SEQ ID NO: 02 AND SEQ ID NO: 04 encoding caroase-01 and caroase 02 respectively are optimalised versions of the genes as picked up, wherein a codon optimalisation has been taken place. Codon optimalisation can be used according to methods known by the person skilled in the art and is especially suitable for improved expression of the gene in a host cell. The invention provides polynucleotide sequences comprising the gene encoding the caroase 01-05 peroxidase. Accordingly, the invention relates to an isolated polynucleotide comprising the nucleotide sequence according to SEQ ID NO: 01-07 or functional equivalents of any of them. The finding of SEQ ID NO: 01-07 on *Marasmius scorodonius* to have bleaching activity was very surprising, especially since the sequences have very low homology to known bleaching enzymes.

More in particular, the invention relates to an isolated polynucleotide hybridisable under stringent conditions, preferably under highly stringent conditions, to a polynucleotide according to SEQ ID NO: 01-07. Advantageously, such polynucleotides may be obtained from fungi, preferably filamentous fungi, in particular from *Marasmius scorodonius*. More specifically, the invention relates to an isolated polynucleotide having a nucleotide sequence according to SEQ ID NO: 01-07.

As used here and hereafter, the terms "gene" and "recombinant gene" refer to nucleic acid molecules which may be isolated from chromosomal DNA, which include an open reading frame encoding a protein, e.g. a *M. scorodonius* bleaching enzyme. A gene may include coding sequences, non-coding sequences, introns and regulatory sequences. Moreover, a gene refers to an isolated nucleic acid molecule as defined herein.

A nucleic acid molecule of the present invention, such as a nucleic acid molecule having the nucleotide sequence of SEQ ID NO: 01-07 or a functional equivalent thereof, can be isolated using standard molecular biology techniques and the sequence information provided herein. For example, using all or portion of the nucleic acid sequence of SEQ ID NO: 01-07 as a hybridization probe, nucleic acid molecules according to the invention can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 01-07 can be isolated by the polymerase chain reaction (PCR) using synthetic oligonucleotide primers designed based upon the sequence information contained in SEQ ID NO: 01-07.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridisable to nucleotide sequences according to the invention can be prepared by standard synthetic techniques, e.g. using an automated DNA synthesizer.

In a preferred embodiment, an isolated nucleic acid molecule of the invention comprises the nucleotide sequence shown in SEQ ID NO: 01-07. This DNA comprises sequences encoding the *M. scorodonius* caroase 01-05 polypeptide according to SEQ ID NO: 08-12, respectively.

In another preferred embodiment, an isolated nucleic acid molecule of the invention comprises a nucleic acid molecule which is a complement of the nucleotide sequence shown in SEQ ID NO: 01-07 or a functional equivalent of these nucleotide sequences.

A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a functional equivalent thereof such as a biologically active fragment or domain, as well as nucleic acid molecules sufficient for use as hybridisation probes to identify nucleic acid molecules encoding a polypeptide of the invention and fragments of such nucleic acid molecules suitable for use as PCR primers for the amplification or mutation of nucleic acid molecules.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a caroase 01-05 nucleic acid molecule, e.g., the coding strand of an caroase 01-05 nucleic acid molecule respectively. Also included within the scope of the invention are the complement strands of the nucleic acid molecules described herein.

Sequencing Errors

The sequence information as provided herein should not be so narrowly construed as to require inclusion of erroneously identified bases. The specific sequences disclosed herein can be readily used to isolate the complete gene from fungi, in particular *M. scorodonius* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

Nucleic Acid Fragments, Probes and Primers

A nucleic acid molecule according to the invention may comprise only a portion or a fragment of the nucleic acid sequence shown in SEQ ID NO: 01-07 for example a fragment which can be used as a probe or primer or a fragment encoding a portion of a caroase 01-05 protein. The nucleotide sequence determined from the cloning of the caroase 01-05 gene and cDNA allows for the generation of probes and primers designed for use in identifying and/or cloning other caroase 01-05 family members, as well as caroase 01-05 homologues from other species. The probe/primer typically comprises substantially purified oligonucleotide which typically comprises a region of nucleotide sequence that hybridizes preferably under highly stringent conditions to at least about 12 or 15, preferably about 18 or 20, preferably about 22 or 25, more preferably about 30, 35, 40, 45, 50, 55, 60, 65, or 75 or more consecutive nucleotides of a nucleotide sequence shown in SEQ ID NO: 01-07 or of a functional equivalent of any of them.

Probes based on the caroase 01-05 nucleotide sequences can be used to detect transcripts or genomic caroase 01-05 sequences encoding the same or homologous proteins for instance in other organisms. In preferred embodiments, the probe further comprises a label group attached thereto, e.g. the label group can be a radioisotope, a fluorescent compound, an enzyme, or an enzyme cofactor. Such probes can also be used as part of a diagnostic test kit for identifying cells which express an caroase 01-05 protein.

Identity & Homology

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wunsch (J. Mol. Biol. (48):444-453 (1970)) algorithm which has been incorporated into the GAP program in the GCG software package (available at www.accelrys.com/solutions/bioinformatician/), using either a Blossom 62 matrix or a PAM250 matrix, and a gap weight of 16, 14, 12, 10, 8, 6, or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity two amino acid or nucleotide sequence is determined using the algorithm of E. Meyers and W. Miller (CABIOS, 4:11-17 (1989) which has been incorporated into the ALIGN program (version 2.0) (available at: vega.igh.cnrs.fr/bin/align-quess.cgi) using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to caroase 01-05 nucleic acid molecules of the invention. BLAST protein searches can be performed with the XBLAST program, score=50, wordlength=3 to obtain amino acid sequences homologous to caroase 01-05 protein molecules of the invention. To obtain gapped alignments for comparison purposes, Gapped BLAST can be utilized as described in Altschul et al., (1997) Nucleic Acids Res. 25(17):3389-3402.

When utilizing BLAST and Gapped BLAST programs, the default parameters of the respective programs (e.g., XBLAST and NBLAST) can be used. See www.ncbi.nlm.nih.gov/.

Hybridization

As used herein, the term "hybridizing" is intended to describe conditions for hybridization and washing under which nucleotide sequences at least about 55%, at least about 40%, at least about 70%, more preferably at least about 80%, even more preferably at least about 85% to 90%, more preferably at least 95% homologous to each other typically remain hybridized to each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

Obtaining Full Length DNA from Other Organisms

In a typical approach, cDNA libraries constructed from other organisms, e.g. filamentous fungi, in particular from the species Marasmius can be screened.

For example, Marasmius strains can be screened for homologous caroase 01-05 polynucleotides by Northern blot analysis. Upon detection of transcripts homologous to polynucleotides according to the invention, cDNA libraries can be constructed from RNA isolated from the appropriate strain, utilizing standard techniques well known to those of skill in the art. Alternatively, a total genomic DNA library can be screened using a probe hybridisable to a caroase 01-05 polynucleotide according to the invention.

Homologous gene sequences can be isolated, for example, by performing PCR using two degenerate oligonucleotide primer pools designed on the basis of nucleotide sequences as taught herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new caroase 01-05 nucleic acid sequence, or a functional equivalent thereof.

The PCR fragment can then be used to isolate a full-length cDNA clone by a variety of known methods. For example, the amplified fragment can be labelled and used to screen a bacteriophage or cosmid cDNA library. Alternatively, the labelled fragment can be used to screen a genomic library.

PCR technology also can be used to isolate full-length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Vectors

Another aspect of the invention pertains to vectors, preferably expression vectors, containing a nucleic acid encoding a caroase 01-05 protein or a functional equivalent thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. caroase 01-05 proteins, mutant forms of caroase 01-05 proteins, fragments, variants or functional equivalents thereof, fusion proteins, etc.).

The recombinant expression vectors of the invention can be designed for expression of caroase 01-05 proteins in prokaryotic or eukaryotic cells. For example, caroase 01-05 proteins can be expressed in fungal cells, bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled person. In a specific embodiment, promoters are preferred that are capable of directing a high expression level of peroxidases in prokaryotes or filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipidmediated transfection or electroporation. Suitable methods for transforming or transfecting host cells can be found in Sambrook, et al. (*Molecular Cloning: A Laboratory Manual*, 2$^{nd}$, ed. Cold Spring Harbor Laboratory, Cold Spring Harbor Laboratory Press, Cold Spring Harbor, N.Y., 1989), Davis et al., *Basic Methods in Molecular Biology* (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methatrexate. Nucleic acid encoding a selectable marker can be introduced into a host cell on the same vector as that encoding an caroase 01-05 protein or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

As indicated, the expression vectors will preferably contain selectable markers. Such markers include dihydrofolate reductase or neomycin resistance for eukarotic cell culture and tetracyline or ampicillin resistance for culturing in *E. coli* and other bacteria. Representative examples of appropriate host include bacterial cells, such as *E. coli, Streptomyces* and *Salmonella typhimurium*; fungal cells, such as yeast; insect cells such as *Drosophila* S2 and *Spodoptera* Sf9; animal cells such as CHO, COS and Bowes melanoma; and plant cells. Appropriate culture media and conditions for the above-described host cells are known in the art.

Among vectors preferred for use in bacteria are pQE70, pQE60 and PQE-9, available from Qiagen; pBS vectors, Phagescript vectors, Bluescript vectors, pNH8A, pNH16A, pNH18A, pNH46A, available from Stratagene; and ptrc99a, pKK223-3, pKK233-3, pDR540, pRIT5 available from Pharmacia. Among preferred eukaryotic vectors are PWLNEO, pSV2CAT, pOG44, pZT1 and pSG available from Stratagene; and pSVK3, pBPV, pMSG and pSVL available from Pharmacia. Other suitable vectors will be readily apparent to the skilled artisan.

Among known bacterial promoters for use in the present invention include *E. coli* lacI and lacZ promoters, the T3 and T7 promoters, the gpt promoter, the lambda PR, PL promoters and the trp promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretation signal may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification.

Host Cells

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like.

Examples of suitable host cells are *Microcystis, Lepista*, for example *L. irina, Cyathus*, for example *C. pallidus, Ganoderma*, for example *G. applanatum, Ischnoderma*, for example *I. benzoinum, Marasmius*, for example *M. scorodonius, Trametes*, for example *T. suaveolens* of *T. versicolor, Cryptococcus*, for example *C. laurentii, Hypomyces*, for example *H. odoratus* or *Phaffia*, for example *P. rhodozyma, Phanerochaete* for example *P. chrysosporium, Lentinula* for example *L. edodes, Coprinus* for example *C. cinereus, Gloeophyllum* for example *G. trabeum, Ophiostoma* for example *O. piliferum, Aspergillus* for example *A. niger, A. oryzae, A. nidulans, Thermomyces*, for example *T. lanuginosa, Sporotrichum*, for example *S. thermophile, Aureobasidium* for example *A. pullulans, Amorphotheca*, for example *A. resinae, Leucosporidium*, for example *L. scottii, Cunninghamella*, for example *C. elegans*.

Especially preferred are cells from filamentous fungi, in particular *Aspergillus*—for example *Aspergillus oryzae* or *Aspergillus niger*—and *Marasmius*—for example *Marasmius scorodonius*—or cells from yeasts such as *Pichia*,—for example *Pichia Pastoris*—or cells from bacteria.

A host cell can be chosen that modulates the expression of the inserted sequences, or modifies and processes the gene product in a specific, desired fashion. Such modifications (e.g. glycosylation) and processing (e.g. cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

Host cells also include, but are not limited to, mammalian cell lines such as CHO, VERO, BHK, HeLa, COS, MDCK, 293, 3T3, WI38, and choroid plexus cell lines. If desired, the polypeptides according to the invention can be produced by a stably-transfected cell line. A number of vectors suitable for stable transfection of mammalian cells are available to the public, methods for constructing such cell lines are also publicly known, e.g., in Ausubel et al. (supra).

Use of the Polypeptides According to the Invention in Industrial Processes

Another aspect of the invention comprises the use of the polypeptides according to the invention or functional equivalents thereof (hereinafter referred to as the bleaching enzyme) in industrial processes, as for example detergents, enzymatic stone-wash processes or food production, for example baking products or dairy products.

The polypeptide according to the invention may be used as an enzyme preparation or produced in situ by a microorganism capable of producing said enzyme. The enzyme preparation can be derived from various sources, for example from plants, animals and microorganisms. Preferably the enzyme preparation is derived from a microorganism, since microorganisms make it possible to obtain the enzyme on an industrial scale in a controlled manner. The enzyme preparation derived from a microorganism can be obtained by classical fermentation processes of a selected microbial strain or by fermentation of a microorganism that overexpresses the polypeptide according to the invention. The microorganism may be a bacterium, a fungus or yeast. For examples of suitable microorganisms as host cells for non-classical fermentation, is referred to the passage above regarding host cells.

The enzyme preparation may also comprise other suitable enzymes, such as for example oxidoreductases, amylases, lipolytic enzymes, hydrolysing enzymes. It has surprisingly been found that especially the combination of an oxidoreductase, for example a hexose oxidase, pyranose oxidase, a maltose oxidising enzyme or glucose oxidase has a synergetic effect on the enzyme activity of the bleaching enzyme according to the invention. The oxidoreductase may be obtained from different sources, including mircoorganisms. Preferably an oxidoreductase from a fungal source is used, for example from a filamentous fungus. A suitable oxidoreductase is glucose oxidase obtainable from for example *Aspergillus* species, such as *Aspergillus niger*. The present invention therefore also relates to a novel enzyme combination of the polypeptide according to the invention with an oxidoreductase.

This effect is even enhanced in case the application in which the enzyme preparation according to the invention is used, has substrate present on which the oxidoreductase is active. In case this is not present, this might also be added to the process. An example of such substrate is the addition of glucose upon the use of a hexose oxidase or glucose oxidase. The present invention therefore also relates to a novel composition comprising the enzyme preparation comprising the polypeptide according to the invention and an oxidoreductase as well as a substrate for the oxidoreductase.

The invention further relates to the use of the novel enzyme combination and novel composition in the production process of a food product according to the invention which is described below.

Surprisingly, was found that the polypeptides according to the invention or their functional equivalents can be used to increase whiteness of at least part of a food product. Preferably, the bleaching polypeptide according to the invention is used in the following food production process. A process for the production of a food product in which an intermediate form of said food products comprises a pigment, which process comprises adding at least one polypeptide according to the invention in an amount that is effective increasing the whiteness of at least part of the food product compared to the food product for which said enzyme is not added during its production.

An intermediate form of the food product is defined herein as any form that occurs during the production process prior to obtaining the final form of the food product. The intermediate form may comprise the individual raw materials used and/or mixture thereof and/or mixtures with additives and/or processing aids, or subsequently processed form thereof.

The polypeptide according to the invention is added in effective amounts. The skilled person can easily determine this effective amount by varying the enzyme dosage and measuring the degradation of pigments and/or the increased whiteness of the final food product. In case the enzyme is capable of converting beta-carotene, the effective amount of enzyme may be expressed in terms of beta-degrading units (e.g. Aziz or Zorn units—see Materials and Methods)

The food product may be made from at least one raw material that is of plant origin, such as wheat flour. The latter is known to contain pigments such as carotenoids (carotenes and xanthophylls) and flavones, which are responsible for, for example, the crumb colour of baked bread. Alternatively, these pigments may originate from other sources than plant raw materials e.g. from milk. Examples of carotenoids are further substances with a carotene backbone, in particular with a beta-carotene or capsanthin backbone, more particularly alpha- and beta-carotene, lutein, lycopene, antheraxanthin, capsanthin, zeaxanthin, violaxanthin, astaxanthin, canthaxanthin, luteoxanthin, neoxanthin, and the respective apocarotenoids.

A preferred food product for the process according to the invention is baked bread and other baked products from wheat flour and/or flours from other cereal origin.

For example, for the baked food product bread, the intermediate forms comprise for example wheat flour, the initial mixture thereof with other bread ingredients such as for example water, salt, yeast and bread improving compositions, the mixed dough, the kneaded dough, the leavened dough and the partially baked dough. In case the enzyme is capable of converting beta-carotene, the enzyme is added to the wheat flour and/or flours from other cereal origin or to any initial mixture with other bread ingredients, in an amount so as to give between 1 and 5000 Zorn units per kg flour, preferably between 5 and 1000 Zorn units per kg flour, more preferably between 10 and 500 Zorn units per kg flour and most preferably between 25 and 250 Zorn units per kg flour. The enzyme may also be added together with or as part of a bread improver mixture with other dough and/or bread improving processing aids known in the art, such as one or more enzymes known in the art (e.g. amylolytic enzymes such as alpha-amylase, beta-amylase, amyloglucosidase, anti-staling maltogenic alpha-amylase, lipolytic enzymes such as lipase, phospholipase, galactolipase, oxidizing enzymes such as glucose oxidase, hexose oxidase, laccase, pyranose oxidase, carbohydrate oxidase, hemicellulolytic enzymes such as xylanase, arabinofuranosidase, cellulolytic enzymes such as endo-glucanases (such as cellulases), cellobiohydrolases, proteases and/or chemical processing aids known in the art such as reducing and oxidizing agents (e.g. ascorbic acid, glutathione), emulsifiers (e.g. DATEM) etceteras.

In some types of noodles, a white product is seen as desirable. For example, for noodles, the intermediate forms comprise for example wheat flour, the initial mixture thereof with water, salt, and other noodle ingredients, the mixed dough and the final noodle product that can be fresh, dried, boiled, steamed and/or fried.

The food product can also be a dairy product. By dairy products is meant products that contain at least 10 wt %, preferably at least 30 wt %, more preferably at least 50 wt %, still more preferably at least 70 wt % or most preferably at least 80 wt % on dry solid basis of components originating from milk, preferably cow's milk. Components originating from milk are for example fats, proteins, for example whey cheese curd and casein, etc. Milk, especially cow's milk, may naturally contain colouring compounds such as carotenoids, for example beta-carotene.

Whiteness plays an important role in for example cheese, butter oil, milk powder or whey products. For example for cheeses like Feta, Mozzarella, Ricotta and blue cheese, for example Danish Blue, Roquefort or Gorgonzola, whiteness is considered desirable. In cheeses wherein milk from goat or sheep is at least partially replaced by cow's milk, the whiteness of the cheese might be a problem because of the β-carotene that is present in cow's milk.

For some cheeses natural colouring agents like annatto or beta-carotene are used as food colouring agents. However, this colouring agent will also be present in the whey. When this whey is further processed into for example baby formula, the colour of the whey product may be undesirable. For the food product soft cheese, the intermediate products comprise e.g. milk, and cheese curd.

Measurement of whiteness of a product can be done visually or a reflection measurement, for example by scanning. In reflection measurement the colors are quantified with three parameters: L-factor (black=0 to white=100), a-factor (green=−60 to red=+60) and b-factor (Blue=−60 to Yellow=+60). In case of carotenoids, the b-factor of the produced product is preferably as closest to 0 as possible, preferably between 10 and 0, more preferably between 5 and 0 and even more preferably lower than 1 and most preferably lower than 0.5. In an additional aspect, the invention provides a food product obtainable by the process of the invention as described hereinbefore. These food products are characterized by at least parts having significantly increased whiteness in comparison with food products obtainable by production processes that do not comprise adding one or more of enzymes capable of converting pigments in the intermediate products.

In a further aspect, the invention provides the use of enzymes capable in converting pigments for bleaching food products, for example flour-based or milk-derived products. Surprisingly, it was found that these enzymes can advantageously be used as a stain remover in household detergents. In particular, the enzymes proved very efficient in removing colored stains, for example grass stains, coffee and tea stains, from both cotton and synthetic (e.g. polyester) fabrics. Furthermore, the enzymes could also be used in enzymatic stone bleaching processes, for example by bleaching the indigo dye of blue jeans to a desired level.

Materials and Methods

Measurement of the Conversion of Beta-Carotene

Measurement of Beta-Carotene Degradation According to Aziz

Enzyme activity can be determined as beta-carotene conversion activity according to A. Ben Aziz (1971), Phytochemistry 10, 1445. One enzyme unit is defined herein as the amount of enzyme that converts 1 microgram of beta-carotene per minute min (further referred to as Aziz-unit).

Measurement of Beta-Carotene Degradation According to Zorn

The enzyme activity can also be determined as beta-carotene conversion activity according to Zorn et al (2003), Appl. Microbiol. Biotechnol. 62:331-336. One enzyme unit is defined herein as the amount of enzyme that converts 1 micromole of beta-carotene per minute (further referred to as Zorn-unit). The assay is carried out as follows: 1.5 ml of enzyme containing sample was pre-incubated in a cuvette at 27° C. for 5 min before 100 µl of beta-carotene stock solution (see further below) was added. If necessary, the concentrated culture supernatant was diluted with a citric acid/phosphate buffer pH 5.5 (this buffer was prepared by mixing 43 ml 0.1 M citric acid with 56 ml 0.2 M $Na_2PO_4$ solutions). The decrease of absorbance was monitored over 15 min at 450 nm and 27° C. using a spectrophotometer in a temperature controlled cell holder. The curve was checked for linearity and the enzyme activity was calculated with the linear part of the curve according to the following equation:

$$\text{enzyme activity}[mU/ml]=(\Delta E \times V_t) \times 10^6/(V_s \times d \times \epsilon)$$

wherein U=enzyme activity unit defined above; $\Delta E$=decrease of absorbance art 450 nm per minute; $V_t$=total volume in cuvette (ml); $V_s$=sample volume in cuvette (ml); $\epsilon$=extinction coefficient of beta-carotene which is 95,000 $M^{-1}$ $cm^{-1}$; d=thickness of cuvette (cm)]

The Aziz enzyme unit can be converted to the Zorn unit by dividing the Aziz units with the molecular weight of beta-carotene=536.85.

Preparation of the Beta-Carotene Stock Solution

The beta-carotene stock solution was prepared as follows: 5 mg beta-carotene and 500 mg Tween-80 were dissolved in 50 mL dichloromethane. The dichloromethane was evaporated at 40° C. and 800 mbar in a rotary evaporator. When nearly all dichloromethane was evaporated, 30 ml water was added and the residual dichloromethane was eliminated in the rotary evaporator and finally in a stream of nitrogen. The resulting solution was filtered and filled up to 50 ml with water in a graduated flask. The solution has to be stored in the cold (refrigerator) and is stable for a few days only.

Bleaching of Food Products

Bleaching was determined after extraction of carotenoids from crumb or dough as indicated by Gelinas, Cereal Chem. 75, 810-184 (1998). Carotenoids were determined via total lipids extraction from crumb of bread as indicated by Gelinas (1998).

Whiteness of a food product can be determined both visually as well as by reflection measurements. Visual inspection can be performed by comparing food products to which a bleaching enzyme is added versus a control without added bleaching enzyme. Reflection measurements can be performed by scanning the food product on a colour scanner (Hewlett Packard Scanjet ADF). These data can be analysed using the programme LabSMART (LabSMART, LLC, Logan Utah, USA).

EXAMPLE 1

Cultivation and Determination of the Activity of the Beta-Carotene Converting Enzyme Obtained from *Marasmius scorodonius*

Cultivation and determination of the activity of the β-carotene converting enzymes caroase-1 and caroase-2 obtained from *Marasmius scorodonius* were carried out as described by Zorn et al. (2003). Hereto, mycelium from the culture collection of *Marasmius scorodonius* (obtainable from the Centraal Bureau voor Schimmelcultures—Utrecht, The Netherlands with deposit number CBS137.83) was used to inoculate agar plates supplemented with emulsified beta-carotene. Incubation of the plates was performed at 24° C. for 14 days. 300 ml shake flasks containing 100 ml of standard nutrition solution (SNL, containing 30 g/liter glucose.$H_2O$; 4.5 g/liter asparagine.$H_2O$; 1.5 g/liter $KH_2PO_4$; 0.5 g/liter $MgSO_4$; 3.0 g/liter yeast extract; 1 ml/liter of a sterilized trace element solution containing 5 mg/l $CuSO_4$*5aq, 80 mg/l $FeCl_3$*6aq, 90 mg/l $ZnSO_4$*7aq, 30 mg/l $MnSO_4$*1aq and 40 mg/l EDTA; the pH was adjusted to 6.0 with 1 N NaOH prior to sterilization) were inoculated with mycelium and were incubated at 24° C. for 7 days in a shaking incubator at 150 rpm. The precultures were checked for the absence of microbial contaminations, homogenised by Ultra Turrax, and used to inoculate the main cultures (250 mL in 500 ml Erlenmeyer flasks). From the second day each day 2 ml samples were drawn, centrifuged to remove the mycelium and the activity was measured in a spectrophotometric assay. After 4 days cultivation, the beta-degrading activity was approximately 0.3 Zorn units per liter cell free supernatant.

EXAMPLE 2

Effect of $H_2O_2$ on the Activity of the Beta-Carotene-Converting Enzymes Caroase-1 and Caroase-2 Obtained from *M. scorodonius*

The effect of 10 microliter 20 mM hydrogen peroxide ($H_2O_2$) is determined in the in vitro assay beta-carotene degradation assay as is described above. Concentrated culture supernatants of *M. scorodonius*, containing caroase-1 and caroase-2 were used. The beta-carotene degradation activity increased from 4.3 to 10.9 mU in the presence of $H_2O_2$. When heat-inactivated enzyme was used, no beta-carotene degradation was observed at all. This clearly demonstrated that $H_2O_2$ stimulates beta-carotene degradation activity by the beta-carotene degrading enzyme.

EXAMPLE 3

Effect of *Aspergillus niger* Glucose Oxidase (GOX) on the Activity of the Caroase-1 and Caroase-2 Obtained from *M. scorodonius*

50 microliter concentrated culture supernatant of *M. scorodonius* was mixed with 1290 microliter of 50 mM sodium acetate buffer (pH 5.5). 160 microliter of a 500 mM glucose solution was added, and the mixture was tempered for 5 min at 27 degrees celsius. The *Aspergillus niger* glucose oxidase was obtained from Fluke. The reaction was started by addition of 0-2 microliter of glucose oxidase stock solution (100 U/ml, corresponding to an activity of 0-200 mU GOX) and 100 microliter beta-carotene solution (preparation as is mentioned under "Materials & Methods"). The decrease of absorption was recorded at 450 nm for 10 min at 27 degrees Celsius (table 1).

TABLE 1

Degradation of beta-carotene by concentrated culture supernatant of *M. scorodonius* in the presence of 50 mM glucose and various doses of GOX.

| GOX (mU) | Activity (mU/ml) | Activity (%) |
|---|---|---|
| 0 | 0.37 | 100 |
| 25 | 1.08 | 295 |
| 50 | 1.41 | 386 |
| 75 | 1.35 | 370 |

TABLE 1-continued

Degradation of beta-carotene by concentrated culture supernatant of *M. scorodonius* in the presence of 50 mM glucose and various doses of GOX.

| GOX (mU) | Activity (mU/ml) | Activity (%) |
|---|---|---|
| 100 | 1.67 | 458 |
| 150 | 0.79 | 216 |

In a second series of experiments, the concentration of glucose was varied, while the amount of glucose oxidase activity was kept constant. Therefore, 50 microliter of concentrated culture supernatant of *M. scorodonius* was mixed with 1434 to 1290 microliter 50 mM sodium acetate buffer (pH 5.5), and 16-160 microliter of 500 mM glucose solution were added (table 2). The mixture was kept for 5 min at 27 degrees Celsius, and the reaction was started by addition of 0-1 microliter GOX (corresponding to an activity of 0 or 100 mU) and 100 microliter of beta-carotene solution.

TABLE 2

Degradation of beta-carotene by concentrated culture supernatant of *M. scorodonius* in the presence of various concentrations of glucose and a dosed glucose oxidase of 100 mU.

| Glucose (mM) | without GOX Activity (mU/ml) | +100 mU GOX Activity (mU/ml) |
|---|---|---|
| 5 | 0.27 | 1.85 |
| 25 | 0.29 | 1.91 |
| 50 | 0.37 | 1.84 |

In the blanks (50 mM glucose, 100 mU GOX, no addition of culture supernatant) no degradation of beta-carotene was observed.

From these experiments it is clear that the presence of GOX in the presence of glucose strongly stimulates beta-carotene degradation by the concentrated supernatant of *M. scorodonius*.

EXAMPLE 4 AND COMPARATIVE EXAMPLES A, B AND C

Pup Loaf Baking Test

In a standard baking process pup loaves were prepared from 200 g wheat flour (a mixture of 160 g of wheat flour (Kolibri®-Meneba, The Netherlands) and 40 gram wheat flour (Ibis®-Meneba, The Netherlands)), 1.4 g Fermipan® dry yeast (DSM Bakery Ingredients, Delft, The Netherlands), 4 g salt, 50 ppm ascorbic acid, 4 ppm fungal α-amylase Bakezyme® P500 (DSM Food Specialties, Delft, The Netherlands), 60 ppm of fungal hemicellulase Bakezyme® HS2000 (DSM Food Specialties, Delft, The Netherlands) and the amount of the beta-carotene degrading enzyme as indicated in Table 3 and 116 ml water in a pin mixer for 6 minutes and 15 seconds. The dough temperature was 28° C. Directly after mixing, the dough is divided into two pieces of 150 g each, rounded and proofed for 45 minutes in a proofing cabinet at 30° C., shaped and panned. After a final proof of 70 minutes at 30° C., the dough was baked for 20 minutes at 225° C.

After 24 hrs of storage in a closed box at room temperature the crumb quality and colour of the baked bread was evaluated by the baker; the amount of carotenoids was determined after extraction of the bread crumb as indicated in Table 4.

TABLE 3

Enzyme dosage (expressed as Zorn units per 200 gram of flour)

| Enzyme from | Assay | Loaf A | Loaf B | Loaf C | Loaf 1 | Loaf 2 |
|---|---|---|---|---|---|---|
| Enzyme active soy flour | Aziz | — | 18.6 | — | — | — |
| Soy enzyme Lipoxygenase 2 | Aziz | — | — | 18.6 | — | — |
| *Marasmius scorodonius* caroase-01 | Zorn | — | — | — | 18.6 | — |
| *Marasmius scorodonius* caroase-02 | Zorn | — | — | — | — | 18.6 |

TABLE 4

Carotenoid content of the loaves and visual identification

| | Loaf A | Loaf B | Loaf C | Loaf 1 | Loaf 2 |
|---|---|---|---|---|---|
| % Carotenoid present | 100 | 8 | 30 | 5 | 6 |
| Visual inspection | Yellowish | White | Off-White | White | White |

From Table 4 can be concluded that by addition of the bleaching enzymes according to the invention to the dough, carotenoids are degraded, resulting in a whiter crumb. The efficiency of the process according to the invention is better than for the used soy enzyme Lipoxygenase 2, and is at least equal to or better than the use of enzyme active soy flour.

EXAMPLE 5

Preparation of Mini Cheeses

Miniature cheeses were produced as described by Shakeel-Ur-Rehman et al. (Protocol for the manufacture of miniature cheeses in Lait, 78 (1998), 607-620). Raw cows milk was pasteurised by heating for 30 minutes at 63° C. The pasteurised milk was transferred to wide mouth plastic centrifuge bottles (200 mL per bottle) and cooled to 31° C. Subsequently, 0.72 ml of starter culture DS 5LT1 (DSM Gist B. V., Delft, The Netherlands) was added to each of the 200 ml of pasteurised milk in the centrifuge bottles and the milk was ripened for 20 minutes. Then, $CaCl_2$ (132 μL of a 1 mol.$L^{-1}$ solution per 200 mL ripened milk) was added, followed by addition of the coagulant (0.04 IMCU per ml). In case the experiment involved the use of caroase-01 and caroase-02, this enzyme was added together with the coagulant.

The milk solutions were held for 40-50 minutes at 31° C. until a coagulum was formed. The coagulum was cut manually by cutters of stretched wire, spaced 1 cm apart on a frame. Healing was allowed for 2 minutes followed by gently stirring for 10 minutes. After that, the temperature was increased gradually to 39° C. over 30 minutes under continuous stirring of the curd/whey mixture. Upon reaching a pH of 6.2 the curd/whey mixtures were centrifuged at room temperature for 60 minutes at 1,700 g. The whey was drained and the curds were held in a water bath at 36° C. The cheeses were inverted every 15 minutes until the pH had decreased to 5.2-5.3 and were then centrifuged at room temperature at 1,700 g for 20 minutes. After further whey drainage the cheese bleaching was determined by scanning. Use of bleaching enzymes caroase-01 and caroase-02 resulted in a whiter cheese.

The invention claimed is:

1. An isolated polypeptide that has the ability to increase whiteness of a food product, wherein the polypeptide is selected from the group consisting of:
   (a) a polypeptide encoded by the polynucleotide comprising the nucleotide sequence of SEQ ID NO: 1, 2, 3, 4, 5, 6 or 7;
   (b) a polypeptide encoded by a polynucleotide which hybridizes under high stringency conditions to the complement of the polynucleotide of (a), and wherein said high stringency conditions comprise hybridizing at 68° C. in 5×SSC, 5×Denhardt's solution and 1.0% SDS and washing in 0.2×SSC and 0.1% SDS at room temperature;
   (c) a polypeptide comprising the amino acid sequence of SEQ ID NO: 8, 9, 10, 11 or 12;
   (d) a polypeptide that is at least 95% identical to the amino acid sequence of SEQ ID NO: 8, 9, 10, 11 or 12; and
   (e) a polypeptide encoded by a polynucleotide comprising a nucleotide sequence that is at least 95% identical to SEQ ID NO: 1, 2, 3, 4, 5, 6 or 7.

2. The isolated polypeptide of claim 1 obtained from *Marasmius scorodonius*.

3. The isolated polypeptide of claim 1, wherein the polypeptide is expressed in an *Aspergillus niger* host cell.

* * * * *

SEQUENCE LISTING

<160> NUMBER OF SEQ ID NOS: 17

<210> SEQ ID NO 1
<211> LENGTH: 1536
<212> TYPE: DNA
<213> ORGANISM: Marasmius scorodonius

<400> SEQUENCE: 1

```
agtatgcggc tcacttacct tcccttgttt gcgggcatcg ccatccagtc tgcatgtgcc      60
tttccaaact tctccaagtc ttccatatta aagcctcgta ggacgaactc cctactaatc     120
aatcccgatg ctcagccaga cctcccgacc gcaaagcagg cttccactgc ggctgcttct     180
gtgggtttga accttaccga catccaagga gacatcttaa tcggtatgaa gaagaacaag     240
gaaatgttct tcttcttcag tattgcagat gccgctgcat tcaaatccca cttgggctcc     300
gctattctcc ctcttatcac ctcgacgcaa cagctgcttg ctgttgccag ccagcctacc     360
accgctgtca accttgcctt ctcccaaacc ggattgaatg cgctggggct tgctgctcaa     420
ggcttggggg actccctctt tgccagtggt cagttcagcg gtgcacagag tctcggcgac     480
ccgggaacct cgaactgggt ccaagcgttc gctggtacag gcatacatgg tgtcttcctt     540
ctcgcatcgg ataccgtcga caacgtgaat gccgagctgt cgcaaatcca gtccatcttg     600
ggaacctcca tcactgaggc gtaccgcctt cagggtgagg ctcgtcccgg cgatcagcaa     660
ggccacgaac atttcggatt catggacgga atcagcaacc ctgccatcga cggattctcc     720
actgcgctgc ctggtcaagc cgttctcagt cccggacttt tcctgctagg agaggacggc     780
gatggttcct cgtcttcgcg tccgtcttgg gcaaaggacg gctctttcct tgctttccgc     840
cagcttcaac agcgtgtccc agagttcaac aagttcctcg ctgacaacgc tgcgctaaca     900
cagggtaacg ctgatcttct cggtgcccga atgatgggac ggtggaaatc tggtgctccg     960
gtcgaccttg cccccaccgc ggatgatgtt gatctcgcta atgaccccca aaggaacaac    1020
aacttcaact ttacccacgc cggttttcacc gagaccactg acgaaactca ctgcccctttc   1080
tccgctcaca tccgtaagac gaaccctcga tcggacttca accccagaa caccaacaac     1140
cacatcatcc gtgctggtat tccttacgga cctgaagtca ctgacgctga gcctcatcc     1200
aacacgtcca gcacggacgc tagcctcgag cgtggcttgg ctttcgttgc ataccaatcg    1260
aacattggca acggcttcgc attccttcaa caggcttggg ttgacaacgc aaacttcttc    1320
ttcgggaaga ccaccccacc tggtgttgac cccatcatcg gctcggttgc tgcgcagaac    1380
aacttcgccc ccaacggtcc ccgtcctgtg tccggactcg accccacaga ttcgaccaag    1440
atcgtcacca taaacaccga cttcgtctct ctcgtggag gagaatactt cttctccccc     1500
tcgctctctg cgatccagaa cacgctttct gtttga                              1536
```

<210> SEQ ID NO 2
<211> LENGTH: 1534
<212> TYPE: DNA
<213> ORGANISM: Artificial sequence
<220> FEATURE:
<223> OTHER INFORMATION: Codon optimised for A. niger host

<400> SEQUENCE: 2

```
atgcgcctca cttacctccc cctgttcgcc ggcatcgcca tccagtccgc ctgcgccttc      60
cctaacttct ccaagagctc catcctgaag cctcgccgca ccaactccct gctgattaac     120
cccgatgccc agcctgatct ccccaccgcc aagcaggcct ccactgccgc tgcttctgtg     180
```

```
ggtctgaact tgaccgatat ccagggcgat atcctcatcg gtatgaagaa gaacaaggag    240
atgttcttct tcttctccat tgctgacgcc gccgccttca agtcccacct gggctccgct    300
attctccccc tcatcacctc tacccagcag ctgttggctg tcgccagcca gcctaccacc    360
gctgtcaacc tcgccttctc ccagaccggt ctgaacgctc tgggtttggc ggctcagggc    420
ctgggtgatt ccctcttcgc ctccggtcag ttcagcggtg ctcagtccct cggcgacccc    480
ggtacctcca actgggtcca ggccttcgcg gtaccggca tccacggtgt cttcctcctc     540
gctagcgaca ccgtcgataa cgtgaacgcc gagctgagcc agattcagag catcttgggt    600
acctccatca ctgaggccta ccgccttcag ggtgaggcgc gtcccggcga ccagcagggc    660
cacgagcact tcggcttcat ggatggtatc agcaaccctg ccatcgacgg cttctccact    720
gctctgcctg tcaggccgt gctctccccc ggtctttttcc tgttgggtga agacggcgac    780
ggctcgtcct cgtctcgtcc tagctgggcg aaggatggat cttttccttgc cttccgccag    840
cttcagcagc gtgtccccga gttcaacaag ttcctcgctg acaacgctgc tcttacccag    900
ggtaacgccg acctcctggg tgcccgtatg atgggccgct ggaagtctgg tgctcccgtc    960
gatcttgccc ccaccgcgga cgacgtcgat ctcgccaacg atccccagcg caacaacaac   1020
ttcaacttca cccacgccgg tttcaccgag accactgacg agactcactg ccccttcagc   1080
gctcacatcc gcaagactaa ccccgctcg gacttcaacc cccagaacac caacaaccac   1140
atcatccgtg ctggtatccc ttacggacct gaagtcactg acgctgaagc ctcttccaac   1200
acttcctcga ctgacgctag cctcgaacgt ggacttgctt tcgttgcgta ccagtccaac   1260
attggcaacg gcttcgcttt cattcagcag aactgggttg acaacgccaa cttcttcttc   1320
ggtaagacca cccctcccgg cattgacccc attatcggtt cgaacgccgc ccagaacaac   1380
ttcgctccca actctcctcg tcccgtttct ggactcgacc ctaccgactc gaccactatc   1440
gtcaccctga acaccgattt cgtggttagc cgtggaggag agtacttctt ctccccctcg   1500
ctttctgcca tccagaacac cttgtctgtt taaa                               1534

<210> SEQ ID NO 3
<211> LENGTH: 1542
<212> TYPE: DNA
<213> ORGANISM: Marasmius scorodonius

<400> SEQUENCE: 3
atgaagcttt tttctgcctc tgttttttgct gctatcgtcg ctagtcacta tgcgtcagcg    60
actgcccaca tcagggctcc caatgtgaag ccaaggagga caagctcact tctgattact   120
cccctcaac agcctccgct tccatctgct caacaggctg caagtgcctc tagcagtgct   180
ggcttgaatc tcaccgacat tcagggtgat attctgatcg gcatgaagaa gaacaaggaa   240
ctattcttct tcttcagtgt caccgacgca gctactttca aggctaagct gggatccgac   300
attcttggac taatcacatc caccgatcag ctacttgcta atgatactca gcctgtcacg   360
gctgtcaacg tcgctttctc tagcactggc ctcaaggcat gggtatcac agatggtctg   420
aaggatcctg tcttcgaggc cggaatgctc agcaacgcag tgagcgactt gagcgatcca   480
gggaccggca attgggtccc tgggtttgtc ggcaccagtg ttcatggcgt tttcctactt   540
gcatcggaca ccattgacaa tgtaaacacc gagccggcca acatccaaac catttttgaat   600
ggctcgatca cggagattca tcgtttacaa ggggaggctc gacccggtga ccagcaaggt   660
cacgaacact ttggattcat ggatggaatc agtaacccgg ccgttgatgg attacacctt   720
ccagcggaaa taagacctgg acaagcttta attccgcctg gtatcatgct ctctcggagag   780
```

```
gcaaacgaca cttttcagaa tgatcgtcct ccgtgggcca agatggttc cttccttgtc    840 ttccgtcaaa tgcaacagcg cgcgcccgag ttcaacaagt tcctgcaaga tcacgctctt    900
aacatgccga atatgacatc cgagcaaggc gctgatctcc ttggtgccag gattgtagga    960
cgatggaaaa gtggtgctcc tattgacctc actccgttgg tcgatgaccc agtgttggct   1020
gctgacaatc agcgaaataa caacttcgac ttttctgacg ccacgaatca gacacgttgc   1080
cctttctctg ctcatatccg caaggctaac ccgcgcggcg atcttggggg tattaataaa   1140
ttcccaaacc aacacataat ccgagcggga attccgtatg acccgaagt taccgacgct   1200 gaaagagcgt caaatagctc tagcactgac cctagtctgg agcgtggtct ggcgtttgtg   1260
gcctatcagt ctaatatcca gaacggattc gtattccttc aaaagaattg ggttgataat   1320
acgaatttct tccgacccgg cactggtgca gatcctctca tcggtacaaa ttctcgtaac   1380
agtggcaccg atgcccccaa cacgcctcgt gtcgtcagcg gcttggatcc taataacgct   1440
acgagcacca tcgaaattga tatcgatttc gtagtttctc gtggaggaga atacttcttc   1500
tcgccctcac tttctgcgat caggactgtg ctttcagtct ag                      1542

<210> SEQ ID NO 4
<211> LENGTH: 1543
<212> TYPE: DNA
<213> ORGANISM: Artificial sequence
<220> FEATURE:
<223> OTHER INFORMATION: Codon optimised for A. niger host

<400> SEQUENCE: 4
atgaagctct ctccgcttc cgttttcgcc gcgatcgtcg cctcgcacta cgcctccgcg     60
actgcccaca tccgcgctcc caacgtgaag ccccgccgca ccaactccct tctgatcact    120 cccctcagc agcctcccct tccctctgct cagcaggctg cctccgcctc cagctccgct    180
ggcctcaacc ttaccgacat tcagggtgac attctgatcg gcatgaagaa gaacaaggaa    240
ctcttcttct tcttctccgt caccgacgcc gctactttca aggctaagct cggatccgac    300
attctcggtc tgatcaccct caccgatcag ctgctcgcta cgacactca gcctgtcacc    360 gctgtcaacg tcgcttttctc tagcactggc ctcaaggcct gggtatcac cgacgatctg    420 aaggatcccg tcttcgaggc cggtatgctc agcaacgccg tgagcgactt gagcgatccc    480
ggtaccggca actgggtccc tggcttcgtc ggcacctccg ttcacggcgt tttcctgctc    540
gcctcggaca ccatcgacaa cgtcaacacc gagctggcca acatccagac cattttgaac    600
ggctcgatca ccgagattca ccgtctgcag ggtgaggctc gtcccggtga ccagcagggt    660
cacgagcact tcggattcat ggacggtatc tccaaccccg ccgttgacgg cttcacccct    720
cccgcggaaa tccgtcctgg acaggctctc attccccccg gtatcatgct ctcggtgag    780 gccaacgaca cttttccagaa cgatcgtcct ccctgggcca aggacggttc cttccttgtc    840
ttccgtcaga tgcagcagcg cgcgcccgag ttcaacaagt tcctgcagga tcacgccctc    900
aacatgccca acatgacctc cgagcagggc gctgatctcc ttggtgcccg cattgttgga    960
cgctggaagt ccggtgctcc tatcgacctc actcccttgg tcgatgaccc cgtgttggcc   1020
gccgacaacc agcgcaacaa caacttcgac ttctctgacg ccaccaacca gacccgttgc   1080
cctttctctg ctcacatccg caaggctaac cccgcggcg atctcggtgg tatcaacaag   1140
ttccccaacc agcacatcat ccgcgccggt attccctacg gtcccgaagt taccgacgct   1200
gagaaggcgt ccaacagctc tagcactgac ccttcgctgg agcgtggtct ggcgttcgtg   1260
gcctaccagt ctaacatcca gaacggattc gtgttccttc agaagaactg ggttgacaac   1320
```

```
accaacttct tccgtcccgg cactggtgtc gatcctctca tcggtaccaa ctctcgtaac    1380
tccggcaccg atgcccccaa cacccctcgt gtcgtcagcg gcttggatcc taacaacgct    1440
accagcacca tcgagatcga tatcgacttc gtcgtttctc gtggaggcga atacttcttc    1500
tcgccctcgc tctctgccat ccgcactgtg ctctccgtct aaa                     1543

<210> SEQ ID NO 5
<211> LENGTH: 1527
<212> TYPE: DNA
<213> ORGANISM: Marasmius scorodonius

<400> SEQUENCE: 5
atgaagcttt tttctgcctc cgttttgct gctatcgtcg ctagtcacta tgtgtcaggg     60
actacccaca tcagggctcc caacgtgaag ccaaggagga caaactcact tctgattact    120 cccctcaac agcctccgct cccatctgct caacaggctg caagtgcctc tagcagtgct    180
ggcttgaatc tcaccgacat tcagggtgat attctgatcg gcatgaagaa gaacaaggaa    240
ctatttttct tcttcagcat caccgacgcc gctactttca aggctaagct aggatccgac    300
attcttgaac taatcacatc gaccaatcag ttactcgccg tcgccactca gcctatcacg    360
gctgtcaacc tcgcgttctc tagcaccggc ctcaaggcat gggtgttaa agatgatttg    420 aatgacaccg ttttcgacgc cgggatgctt agcaacgcag tgagcgattt gagcgatccc    480
ggaaccggca attgggtacc tggcttcgta ggtaccgctg ttcatggcgt tttcctactt    540
gcatcggaca ctcttgacaa cgtgaacgcg gaactggcca acattcaaac aatcttgaat    600
ggctcgatta cggagattca tcgtctgcag ggagaggctc gacccggtga tcaacaaggt    660
cacgaacact ttggattcat ggatgggatc agtaacccag ccatcgatgg attttcgacc    720
cggcttcccg gacaagcttt acttccgcct ggacttatgt ttctcggaga ggcaaacgac    780
actgtttcgc gtcctccgtg ggccaaagat ggatccttcc ttgtcttccg gcaaatgcaa    840
cagcgtgtac ctgaattcga caaattcctg caagaccacg ctcttaacat gccgaatatg    900
acatctgaac aaggtgctga gctcctaggc tccaggatgg tggggcgatg gaaaagtggt    960
gctccaatcg atctcactcc gttggtcgat gacccggagt tggctgctga ccctcagcga    1020
aataacaact tcgactttc tgacgccacg aatcagacac gttgcccttt ctctgctcat    1080
atccgtaaga ctaaccgcg cgctgatctt ggggggtattg ataacttccc gacgcgtcac    1140
ataatccgag cgggaattcc atatggaccc gaagttaccg acgctgaaaa agcgtcaaat    1200
agctctagca cagaccctag tctggagcgt ggtctggcgt ttgtggccta tcagtctaat    1260
atcaagaacg cattcgtatt ccttcaacag acttgggttg ataatgcgaa cttctttagg    1320
accaacactg gggcagatcc tatcataggt accctgtcga caagaacgg caatctcccc    1380 aacacgcctc gtaatgttag cggtctggat cctaacaatc ccaccggccc cccaccgaa    1440 atcgaccttg actttgttgt ttctcgtggt ggagaatact tcttttcgcc ctccctttcc    1500
gcgatcagga ctgtgctttc agtctag                                       1527

<210> SEQ ID NO 6
<211> LENGTH: 1542
<212> TYPE: DNA
<213> ORGANISM: Marasmius scorodonius

<400> SEQUENCE: 6
atgaagcttt tttctgcctc cgttttgct gctatcgtcg ctagtcacta tgcgtcagcg     60
actgcccaca tcagggctcc caatgtgaag ccaaggagga caaactcact tctgattact    120
```

```
cccccctcaac agcctccgct tccatctgct caacaggctg caagtgcctc tagcagtgct      180
ggcttgaatc tcaccgacat tcagggtgat attctgatcg gcatgaagaa gaacaaggaa      240
ctattcttct tcttcagtgt caccgacgca gctactttca aggctaagct gggatccgac      300
attcttggac taatcacatc caccgatcag ctacttgcta atgatactca gcctgtcacg      360
gctgtcaacg tcactttctc tagcactggc ctcaaggcat gggtatcac agatgatctg       420
aaggatcctg tcttcgaggc cggaatgctc agcaacgcag tgagcgactt gagcgatcca      480
gggaccggca attgggtccc tgggtttgtc ggcaccagtg ttcatggcgt tttcctactt      540
gcatcggaca ccattgacaa tgtaaacacc gagctggcca acatccaaac catttcgaat      600
ggctcgatca cggagattca tcgtttacaa ggggaggctc gacccggtga ccagcaaggt      660
cacgaacact ttggattcat ggatggaatc agtaacccgg ccgttgatgg atttacacct      720
ccagcggaaa taagacctgg acaagcttta attccgcctg gtatcatgct ctcggagag       780
gcaaacgaca cttttcagaa tgatcgtcct ccgtgggcca agatggttc cttccttgtc       840
ttccgtcaaa tgcaacagcg cgtgcccgag ttcaacaagt tcctgcaaga tcacgctctt      900
aacatgccga atatgacatc cgagcaaggc gctgatctcc ttggtgccag gattgtagga      960
cgatggaaaa gtggtgctcc tattgacctc actccgttgg tcgatgaccc agtgttggct     1020
gctgacaatc agcgaaataa caacttcgac ttttctgtcg ccacgaatca gacacgttgc     1080
cctttctctg ctcatatccg caaggctaac ccgcgcggcg atcttggggg tattaataaa     1140
ttcccaaacc aacacataat ccgagcggga attccgtatg acccgaagt taccgacgct      1200
gaaaaagcgt caaatagctc tagcactgac cctagtctgg agcgtggtct ggcgtttgtg     1260
gcctatcagt ctaatatcca gaacggattc gtattccttc aaaagaattg ggttgataat     1320
acgaatttct tccgacccgg cactggtgta gatcctctca tcggtacaaa ttctcgtaac     1380
agtggcaccg atgcccccaa cacgcctcgt gtcgtcagcg gcttggatcc taataacgct     1440
acgagcacca tcgaaattga tatcgatttc gtagtttctc gtggaggaga atacttcttc     1500
tcgccctcac tttctgcgat caggactgtg cttttcagtct ag                       1542
```

<210> SEQ ID NO 7
<211> LENGTH: 1536
<212> TYPE: DNA
<213> ORGANISM: Marasmius scorodonius

<400> SEQUENCE: 7

```
agtatgcggc tcacttacct tcccttgttt gcgggcatcg ccatccagtc tgcatgtgcc       60
tttccaaact tctctaagtc ttccatatta aagcctcgta ggacgaactc cctactaatc      120
aatcccgatg ctcagccaga cctcccgacc gcaaagcagg cttccactgc ggctgcttct      180
gtgggtttga accttaccga catccaagga gacatcttaa tcggtatgaa gaagaacaag      240
gaaatgttct tcttcttcag tattgcagat gccgctgcat tcaaatccca cttgggctcc      300
gctattctcc ctcttatcgc ctcgacgcaa cagctgcttg ctgttgccag ccagcctacc      360
accgctgtca accttgcctt ctcccaaacc ggattgaatg cgctgggcgt tgctgctcaa      420
ggcttggggg actccctctt tgccagtggt cagttcagcg gtgcacagag tctcggcgac      480
ccggaacct cgaactgggt ccaagcgttc gctggtacag gcatacatgg tgtcttcctt       540
ctcgcatcgg ataccgtcga caacgtgaat gccgagctgt cgcaaatcca gtccatcttg      600
ggaacctcca tcactgaggc gtaccgcctt cagggtgagg ctcgtcccgg cgatcagcaa      660
ggccacgaac atttcggatt catggacgga atcagcaacc ctgccatcga cggattctcc      720
```

-continued

```
actgcgctgc ctggtcaagc cgttctcagt cccggacttt tcctgctagg agaggacggc      780
gatggttcct cgtcttcgcg tccgtcttgg gcaaaggacg gctctttcct tgctttccgc      840
cagcttcaac agcgtgtccc agagttcaac aagttcctcg ctgacaacgc tgcgctaaca      900
cagggtaacg ctgatcttct cggtgcccga atgatgggac ggtggaaatc tggtgctccg      960
gtcgaccttg cccccaccgc ggatgatgtt gatctcgcta atgaccccca aggaacaac      1020 aacttcaact ttacccacgc cggttttcacc gagaccactg acgaaactca ctgcccctt c     1080 tccgctcaca tccgtaagac gaaccctcga tcggacttca accccagaa caccaacaac      1140 cacatcatcc gtgctggtat tccttacgga cctgaagtca ctgacgctga agcctcatcc      1200
aacacgtcca gcacggacgc tagcctcgag cgtggcttgg ctttcgttgc ataccaatcg      1260
aacattggca acggcttcgc attccttcaa caggcttggg ttgacaacgc aaacttcttc      1320
ttcggaaaga ccacccccacc tggtgttgac cccatcatcg gctcggttgc tgcgcagaac      1380
aacttcgccc ccaacggtcc ccgtcctgtg tccggacttg accccacaga ttcgaccaag      1440
atcgtcacca taaacaccga cttcgtctct ctcgtggag gagaatactt cttctccccc       1500
tcgctctctg cgatccagaa cacgctttct gtttga                                1536
```

<210> SEQ ID NO 8
<211> LENGTH: 510
<212> TYPE: PRT
<213> ORGANISM: Marasmius scorodonius

<400> SEQUENCE: 8

```
Met Arg Leu Thr Tyr Leu Pro Leu Phe Ala Gly Ile Ala Ile Gln Ser
1               5                   10                  15

Ala Cys Ala Phe Pro Asn Phe Ser Lys Ser Ser Ile Leu Lys Pro Arg
            20                  25                  30

Arg Thr Asn Ser Leu Leu Ile Asn Pro Asp Ala Gln Pro Asp Leu Pro
        35                  40                  45

Thr Ala Lys Gln Ala Ser Thr Ala Ala Ala Ser Val Gly Leu Asn Leu
    50                  55                  60

Thr Asp Ile Gln Gly Asp Ile Leu Ile Gly Met Lys Lys Asn Lys Glu
65                  70                  75                  80

Met Phe Phe Phe Phe Ser Ile Ala Asp Ala Ala Ala Phe Lys Ser His
                85                  90                  95

Leu Gly Ser Ala Ile Leu Pro Leu Ile Thr Ser Thr Gln Gln Leu Leu
            100                 105                 110

Ala Val Ala Ser Gln Pro Thr Thr Ala Val Asn Leu Ala Phe Ser Gln
        115                 120                 125

Thr Gly Leu Asn Ala Leu Gly Leu Ala Ala Gln Gly Leu Gly Asp Ser
    130                 135                 140

Leu Phe Ala Ser Gly Gln Phe Ser Gly Ala Gln Ser Leu Gly Asp Pro
145                 150                 155                 160

Gly Thr Ser Asn Trp Val Gln Ala Phe Ala Gly Thr Gly Ile His Gly
                165                 170                 175

Val Phe Leu Leu Ala Ser Asp Thr Val Asp Asn Val Asn Ala Glu Leu
            180                 185                 190

Ser Gln Ile Gln Ser Ile Leu Gly Thr Ser Ile Thr Glu Ala Tyr Arg
        195                 200                 205

Leu Gln Gly Glu Ala Arg Pro Gly Asp Gln Gln Gly His Glu His Phe
    210                 215                 220

Gly Phe Met Asp Gly Ile Ser Asn Pro Ala Ile Asp Gly Phe Ser Thr
225                 230                 235                 240
```

```
Ala Leu Pro Gly Gln Ala Val Leu Ser Pro Gly Leu Phe Leu Leu Gly
                245                 250                 255

Glu Asp Gly Asp Gly Ser Ser Ser Arg Pro Ser Trp Ala Lys Asp
            260                 265                 270

Gly Ser Phe Leu Ala Phe Arg Gln Leu Gln Gln Arg Val Pro Glu Phe
                275                 280                 285

Asn Lys Phe Leu Ala Asp Asn Ala Ala Leu Thr Gln Gly Asn Ala Asp
        290                 295                 300

Leu Leu Gly Ala Arg Met Met Gly Arg Trp Lys Ser Gly Ala Pro Val
305                 310                 315                 320

Asp Leu Ala Pro Thr Ala Asp Val Asp Leu Ala Asn Asp Pro Gln
                325                 330                 335

Arg Asn Asn Asn Phe Asn Phe Thr His Ala Gly Phe Thr Glu Thr Thr
                340                 345                 350

Asp Glu Thr His Cys Pro Phe Ser Ala His Ile Arg Lys Thr Asn Pro
                355                 360                 365

Arg Ser Asp Phe Asn Pro Gln Asn Thr Asn Asn His Ile Ile Arg Ala
        370                 375                 380

Gly Ile Pro Tyr Gly Pro Glu Val Thr Asp Ala Glu Ala Ser Ser Asn
385                 390                 395                 400

Thr Ser Ser Thr Asp Ala Ser Leu Glu Arg Gly Leu Ala Phe Val Ala
                405                 410                 415

Tyr Gln Ser Asn Ile Gly Asn Gly Phe Ala Phe Leu Gln Gln Ala Trp
                420                 425                 430

Val Asp Asn Ala Asn Phe Phe Phe Gly Lys Thr Thr Pro Pro Gly Val
                435                 440                 445

Asp Pro Ile Ile Gly Ser Val Ala Ala Gln Asn Asn Phe Ala Pro Asn
        450                 455                 460

Gly Pro Arg Pro Val Ser Gly Leu Asp Pro Thr Asp Ser Thr Lys Ile
465                 470                 475                 480

Val Thr Ile Asn Thr Asp Phe Val Ser Arg Gly Gly Glu Tyr Phe
                485                 490                 495

Phe Ser Pro Ser Leu Ser Ala Ile Gln Asn Thr Leu Ser Val
                500                 505                 510

<210> SEQ ID NO 9
<211> LENGTH: 513
<212> TYPE: PRT
<213> ORGANISM: Marasmius scorodonius

<400> SEQUENCE: 9

Met Lys Leu Phe Ser Ala Ser Val Phe Ala Ala Ile Val Ala Ser His
1               5                   10                  15

Tyr Ala Ser Ala Thr Ala His Ile Arg Ala Pro Asn Val Lys Pro Arg
                20                  25                  30

Arg Thr Ser Ser Leu Leu Ile Thr Pro Pro Gln Gln Pro Pro Leu Pro
            35                  40                  45

Ser Ala Gln Gln Ala Ala Ser Ser Ser Ala Gly Leu Asn Leu
        50                  55                  60

Thr Asp Ile Gln Gly Asp Ile Leu Ile Gly Met Lys Lys Asn Lys Glu
65                  70                  75                  80

Leu Phe Phe Phe Phe Ser Val Thr Asp Ala Ala Thr Phe Lys Ala Lys
                85                  90                  95

Leu Gly Ser Asp Ile Leu Gly Leu Ile Thr Ser Thr Asp Gln Leu Leu
                100                 105                 110
```

```
Ala Asn Asp Thr Gln Pro Val Thr Ala Val Asn Val Ala Phe Ser Ser
            115                 120                 125

Thr Gly Leu Lys Ala Leu Gly Ile Thr Asp Gly Leu Lys Asp Pro Val
        130                 135                 140

Phe Glu Ala Gly Met Leu Ser Asn Ala Val Ser Asp Leu Ser Asp Pro
145                 150                 155                 160

Gly Thr Gly Asn Trp Val Pro Gly Phe Val Gly Thr Ser Val His Gly
                165                 170                 175

Val Phe Leu Leu Ala Ser Asp Thr Ile Asp Asn Val Asn Thr Glu Pro
            180                 185                 190

Ala Asn Ile Gln Thr Ile Leu Asn Gly Ser Ile Thr Glu Ile His Arg
        195                 200                 205

Leu Gln Gly Glu Ala Arg Pro Gly Asp Gln Gln Gly His Glu His Phe
    210                 215                 220

Gly Phe Met Asp Gly Ile Ser Asn Pro Ala Val Asp Gly Phe Thr Pro
225                 230                 235                 240

Pro Ala Glu Ile Arg Pro Gly Gln Ala Leu Ile Pro Pro Gly Ile Met
                245                 250                 255

Leu Leu Gly Glu Ala Asn Asp Thr Phe Gln Asn Asp Arg Pro Pro Trp
            260                 265                 270

Ala Lys Asp Gly Ser Phe Leu Val Phe Arg Gln Met Gln Gln Arg Ala
        275                 280                 285

Pro Glu Phe Asn Lys Phe Leu Gln Asp His Ala Leu Asn Met Pro Asn
    290                 295                 300

Met Thr Ser Glu Gln Gly Ala Asp Leu Leu Gly Ala Arg Ile Val Gly
305                 310                 315                 320

Arg Trp Lys Ser Gly Ala Pro Ile Asp Leu Thr Pro Leu Val Asp Asp
                325                 330                 335

Pro Val Leu Ala Ala Asp Asn Gln Arg Asn Asn Asn Phe Asp Phe Ser
            340                 345                 350

Asp Ala Thr Asn Gln Thr Arg Cys Pro Phe Ser Ala His Ile Arg Lys
        355                 360                 365

Ala Asn Pro Arg Gly Asp Leu Gly Gly Ile Asn Lys Phe Pro Asn Gln
    370                 375                 380

His Ile Ile Arg Ala Gly Ile Pro Tyr Gly Pro Glu Val Thr Asp Ala
385                 390                 395                 400

Glu Arg Ala Ser Asn Ser Ser Thr Asp Pro Ser Leu Glu Arg Gly
                405                 410                 415

Leu Ala Phe Val Ala Tyr Gln Ser Asn Ile Gln Asn Gly Phe Val Phe
            420                 425                 430

Leu Gln Lys Asn Trp Val Asp Asn Thr Asn Phe Phe Arg Pro Gly Thr
        435                 440                 445

Gly Ala Asp Pro Leu Ile Gly Thr Asn Ser Arg Asn Ser Gly Thr Asp
    450                 455                 460

Ala Pro Asn Thr Pro Arg Val Val Ser Gly Leu Asp Pro Asn Asn Ala
465                 470                 475                 480

Thr Ser Thr Ile Glu Ile Asp Ile Asp Phe Val Val Ser Arg Gly Gly
                485                 490                 495

Glu Tyr Phe Phe Ser Pro Ser Leu Ser Ala Ile Arg Thr Val Leu Ser
            500                 505                 510

Val
```

<210> SEQ ID NO 10

```
<211> LENGTH: 508
<212> TYPE: PRT
<213> ORGANISM: Marasmius scorodonius

<400> SEQUENCE: 10

Met Lys Leu Phe Ser Ala Ser Val Phe Ala Ala Ile Val Ala Ser His
1               5                   10                  15

Tyr Val Ser Gly Thr Thr His Ile Arg Ala Pro Asn Val Lys Pro Arg
            20                  25                  30

Arg Thr Asn Ser Leu Leu Ile Thr Pro Pro Gln Gln Pro Pro Leu Pro
        35                  40                  45

Ser Ala Gln Gln Ala Ala Ser Ala Ser Ser Ser Ala Gly Leu Asn Leu
    50                  55                  60

Thr Asp Ile Gln Gly Asp Ile Leu Ile Gly Met Lys Lys Asn Lys Glu
65                  70                  75                  80

Leu Phe Phe Phe Phe Ser Ile Thr Asp Ala Ala Thr Phe Lys Ala Lys
                85                  90                  95

Leu Gly Ser Asp Ile Leu Glu Leu Ile Thr Ser Thr Asn Gln Leu Leu
            100                 105                 110

Ala Val Ala Thr Gln Pro Ile Thr Ala Val Asn Leu Ala Phe Ser Ser
        115                 120                 125

Thr Gly Leu Lys Ala Leu Gly Val Lys Asp Asp Leu Asn Asp Thr Val
130                 135                 140

Phe Asp Ala Gly Met Leu Ser Asn Ala Val Ser Asp Leu Ser Asp Pro
145                 150                 155                 160

Gly Thr Gly Asn Trp Val Pro Gly Phe Val Gly Thr Ala Val His Gly
            165                 170                 175

Val Phe Leu Leu Ala Ser Asp Thr Leu Asp Asn Val Asn Ala Glu Leu
        180                 185                 190

Ala Asn Ile Gln Thr Ile Leu Asn Gly Ser Ile Thr Glu Ile His Arg
    195                 200                 205

Leu Gln Gly Glu Ala Arg Pro Gly Asp Gln Gln Gly His Glu His Phe
210                 215                 220

Gly Phe Met Asp Gly Ile Ser Asn Pro Ala Ile Asp Gly Phe Ser Thr
225                 230                 235                 240

Arg Leu Pro Gly Gln Ala Leu Leu Pro Gly Leu Met Phe Leu Gly
            245                 250                 255

Glu Ala Asn Asp Thr Val Ser Arg Pro Pro Trp Ala Lys Asp Gly Ser
            260                 265                 270

Phe Leu Val Phe Arg Gln Met Gln Gln Arg Val Pro Glu Phe Asp Lys
        275                 280                 285

Phe Leu Gln Asp His Ala Leu Asn Met Pro Asn Met Thr Ser Glu Gln
    290                 295                 300

Gly Ala Glu Leu Leu Gly Ser Arg Met Val Gly Arg Trp Lys Ser Gly
305                 310                 315                 320

Ala Pro Ile Asp Leu Thr Pro Leu Val Asp Pro Glu Leu Ala Ala
            325                 330                 335

Asp Pro Gln Arg Asn Asn Asn Phe Asp Phe Ser Asp Ala Thr Asn Gln
        340                 345                 350

Thr Arg Cys Pro Phe Ser Ala His Ile Arg Lys Thr Asn Pro Arg Ala
    355                 360                 365

Asp Leu Gly Gly Ile Asp Asn Phe Pro Thr Arg His Ile Ile Arg Ala
370                 375                 380

Gly Ile Pro Tyr Gly Pro Glu Val Thr Asp Ala Glu Lys Ala Ser Asn
385                 390                 395                 400
```

Ser Ser Ser Thr Asp Pro Ser Leu Glu Arg Gly Leu Ala Phe Val Ala
            405                 410                 415

Tyr Gln Ser Asn Ile Lys Asn Ala Phe Val Phe Leu Gln Gln Thr Trp
            420                 425                 430

Val Asp Asn Ala Asn Phe Phe Arg Thr Asn Thr Gly Ala Asp Pro Ile
            435                 440                 445

Ile Gly Thr Leu Ser Asn Lys Asn Gly Asn Leu Pro Asn Thr Pro Arg
450                 455                 460

Asn Val Ser Gly Leu Asp Pro Asn Asn Pro Thr Gly Pro Pro Thr Glu
465                 470                 475                 480

Ile Asp Leu Asp Phe Val Ser Arg Gly Glu Tyr Phe Phe Ser
            485                 490                 495

Pro Ser Leu Ser Ala Ile Arg Thr Val Leu Ser Val
            500                 505

<210> SEQ ID NO 11
<211> LENGTH: 513
<212> TYPE: PRT
<213> ORGANISM: Marasmius scorodonius

<400> SEQUENCE: 11

Met Lys Leu Phe Ser Ala Ser Val Phe Ala Ala Ile Val Ala Ser His
1               5                   10                  15

Tyr Ala Ser Ala Thr Ala His Ile Arg Ala Pro Asn Val Lys Pro Arg
            20                  25                  30

Arg Thr Asn Ser Leu Leu Ile Thr Pro Pro Gln Pro Pro Leu Pro
            35                  40                  45

Ser Ala Gln Gln Ala Ala Ser Ala Ser Ser Ala Gly Leu Asn Leu
50                  55                  60

Thr Asp Ile Gln Gly Asp Ile Leu Ile Gly Met Lys Lys Asn Lys Glu
65                  70                  75                  80

Leu Phe Phe Phe Phe Ser Val Thr Asp Ala Ala Thr Phe Lys Ala Lys
            85                  90                  95

Leu Gly Ser Asp Ile Leu Gly Leu Ile Thr Ser Thr Asp Gln Leu Leu
            100                 105                 110

Ala Asn Asp Thr Gln Pro Val Thr Ala Val Asn Val Thr Phe Ser Ser
            115                 120                 125

Thr Gly Leu Lys Ala Leu Gly Ile Thr Asp Asp Leu Lys Asp Pro Val
            130                 135                 140

Phe Glu Ala Gly Met Leu Ser Asn Ala Val Ser Asp Leu Ser Asp Pro
145                 150                 155                 160

Gly Thr Gly Asn Trp Val Pro Gly Phe Val Gly Thr Ser Val His Gly
            165                 170                 175

Val Phe Leu Leu Ala Ser Asp Thr Ile Asp Asn Val Asn Thr Glu Leu
            180                 185                 190

Ala Asn Ile Gln Thr Ile Ser Asn Gly Ser Ile Thr Glu Ile His Arg
            195                 200                 205

Leu Gln Gly Glu Ala Arg Pro Gly Asp Gln Gly His Glu His Phe
            210                 215                 220

Gly Phe Met Asp Gly Ile Ser Asn Pro Ala Val Asp Gly Phe Thr Pro
225                 230                 235                 240

Pro Ala Glu Ile Arg Pro Gly Gln Ala Leu Ile Pro Pro Gly Ile Met
            245                 250                 255

Leu Leu Gly Glu Ala Asn Asp Thr Phe Gln Asn Asp Arg Pro Pro Trp
            260                 265                 270

Ala Lys Asp Gly Ser Phe Leu Val Phe Arg Gln Met Gln Arg Val
        275                 280                 285

Pro Glu Phe Asn Lys Phe Leu Gln Asp His Ala Leu Asn Met Pro Asn
        290                 295                 300

Met Thr Ser Glu Gln Gly Ala Asp Leu Leu Gly Ala Arg Ile Val Gly
305                 310                 315                 320

Arg Trp Lys Ser Gly Ala Pro Ile Asp Leu Thr Pro Leu Val Asp Asp
                325                 330                 335

Pro Val Leu Ala Ala Asp Asn Gln Arg Asn Asn Asn Phe Asp Phe Ser
        340                 345                 350

Val Ala Thr Asn Gln Thr Arg Cys Pro Phe Ser Ala His Ile Arg Lys
        355                 360                 365

Ala Asn Pro Arg Gly Asp Leu Gly Gly Ile Asn Lys Phe Pro Asn Gln
        370                 375                 380

His Ile Ile Arg Ala Gly Ile Pro Tyr Gly Pro Glu Val Thr Asp Ala
385                 390                 395                 400

Glu Lys Ala Ser Asn Ser Ser Thr Asp Pro Ser Leu Glu Arg Gly
                405                 410                 415

Leu Ala Phe Val Ala Tyr Gln Ser Asn Ile Gln Asn Gly Phe Val Phe
        420                 425                 430

Leu Gln Lys Asn Trp Val Asp Asn Thr Asn Phe Phe Arg Pro Gly Thr
        435                 440                 445

Gly Val Asp Pro Leu Ile Gly Thr Asn Ser Arg Asn Ser Gly Thr Asp
450                 455                 460

Ala Pro Asn Thr Pro Arg Val Val Ser Gly Leu Asp Pro Asn Asn Ala
465                 470                 475                 480

Thr Ser Thr Ile Glu Ile Asp Ile Asp Phe Val Val Ser Arg Gly Gly
                485                 490                 495

Glu Tyr Phe Phe Ser Pro Ser Leu Ser Ala Ile Arg Thr Val Leu Ser
                500                 505                 510

Val

<210> SEQ ID NO 12
<211> LENGTH: 510
<212> TYPE: PRT
<213> ORGANISM: Marasmius scorodonius

<400> SEQUENCE: 12

Met Arg Leu Thr Tyr Leu Pro Leu Phe Ala Gly Ile Ala Ile Gln Ser
1               5                   10                  15

Ala Cys Ala Phe Pro Asn Phe Ser Lys Ser Ser Ile Leu Lys Pro Arg
            20                  25                  30

Arg Thr Asn Ser Leu Leu Ile Asn Pro Asp Ala Gln Pro Asp Leu Pro
        35                  40                  45

Thr Ala Lys Gln Ala Ser Thr Ala Ala Ser Val Gly Leu Asn Leu
        50                  55                  60

Thr Asp Ile Gln Gly Asp Ile Leu Ile Gly Met Lys Lys Asn Lys Glu
65                  70                  75                  80

Met Phe Phe Phe Ser Ile Ala Asp Ala Ala Phe Lys Ser His
                85                  90                  95

Leu Gly Ser Ala Ile Leu Pro Leu Ile Ala Ser Thr Gln Gln Leu Leu
            100                 105                 110

Ala Val Ala Ser Gln Pro Thr Thr Ala Val Asn Leu Ala Phe Ser Gln
        115                 120                 125

```
Thr Gly Leu Asn Ala Leu Gly Leu Ala Ala Gln Gly Leu Gly Asp Ser
            130                 135                 140

Leu Phe Ala Ser Gly Gln Phe Ser Gly Ala Gln Ser Leu Gly Asp Pro
145                 150                 155                 160

Gly Thr Ser Asn Trp Val Gln Ala Phe Ala Gly Thr Gly Ile His Gly
                165                 170                 175

Val Phe Leu Leu Ala Ser Asp Thr Val Asp Asn Val Asn Ala Glu Leu
            180                 185                 190

Ser Gln Ile Gln Ser Ile Leu Gly Thr Ser Ile Thr Glu Ala Tyr Arg
        195                 200                 205

Leu Gln Gly Glu Ala Arg Pro Gly Asp Gln Gln Gly His Glu His Phe
210                 215                 220

Gly Phe Met Asp Gly Ile Ser Asn Pro Ala Ile Asp Gly Phe Ser Thr
225                 230                 235                 240

Ala Leu Pro Gly Gln Ala Val Leu Ser Pro Gly Leu Phe Leu Leu Gly
                245                 250                 255

Glu Asp Gly Asp Gly Ser Ser Ser Arg Pro Ser Trp Ala Lys Asp
            260                 265                 270

Gly Ser Phe Leu Ala Phe Arg Gln Leu Gln Arg Val Pro Glu Phe
        275                 280                 285

Asn Lys Phe Leu Ala Asp Asn Ala Ala Leu Thr Gln Gly Asn Ala Asp
290                 295                 300

Leu Leu Gly Ala Arg Met Met Gly Arg Trp Lys Ser Gly Ala Pro Val
305                 310                 315                 320

Asp Leu Ala Pro Thr Ala Asp Asp Val Asp Leu Ala Asn Asp Pro Gln
                325                 330                 335

Arg Asn Asn Asn Phe Asn Phe Thr His Ala Gly Phe Thr Glu Thr Thr
            340                 345                 350

Asp Glu Thr His Cys Pro Phe Ser Ala His Ile Arg Lys Thr Asn Pro
        355                 360                 365

Arg Ser Asp Phe Asn Pro Gln Asn Thr Asn Asn His Ile Ile Arg Ala
370                 375                 380

Gly Ile Pro Tyr Gly Pro Glu Val Thr Asp Ala Glu Ala Ser Ser Asn
385                 390                 395                 400

Thr Ser Ser Thr Asp Ala Ser Leu Glu Arg Gly Leu Ala Phe Val Ala
                405                 410                 415

Tyr Gln Ser Asn Ile Gly Asn Gly Phe Ala Phe Leu Gln Gln Ala Trp
            420                 425                 430

Val Asp Asn Ala Asn Phe Phe Phe Gly Lys Thr Thr Pro Pro Gly Val
        435                 440                 445

Asp Pro Ile Ile Gly Ser Val Ala Ala Gln Asn Asn Phe Ala Pro Asn
450                 455                 460

Gly Pro Arg Pro Val Ser Gly Leu Asp Pro Thr Asp Ser Thr Lys Ile
465                 470                 475                 480

Val Thr Ile Asn Thr Asp Phe Val Ser Ser Arg Gly Gly Glu Tyr Phe
                485                 490                 495

Phe Ser Pro Ser Leu Ser Ala Ile Gln Asn Thr Leu Ser Val
            500                 505                 510

<210> SEQ ID NO 13
<211> LENGTH: 20
<212> TYPE: PRT
<213> ORGANISM: Marasmius scorodonius

<400> SEQUENCE: 13
```

-continued

```
Gly Leu Asn Leu Thr Asp Ile Gln Gly Asp Ile Leu Ile Gly Met Lys
1               5                   10                  15

Lys Asn Lys Glu
            20

<210> SEQ ID NO 14
<211> LENGTH: 22
<212> TYPE: PRT
<213> ORGANISM: Marasmius scorodonius

<400> SEQUENCE: 14

Ala Arg Pro Gly Asp Gln Gln Gly His Glu His Phe Gly Phe Met Asp
1               5                   10                  15

Gly Ile Ser Asn Pro Ala
            20

<210> SEQ ID NO 15
<211> LENGTH: 17
<212> TYPE: PRT
<213> ORGANISM: Marasmius scorodonius

<400> SEQUENCE: 15

His Ile Ile Arg Ala Gly Ile Pro Tyr Gly Pro Glu Val Thr Asp Ala
1               5                   10                  15

Glu

<210> SEQ ID NO 16
<211> LENGTH: 12
<212> TYPE: PRT
<213> ORGANISM: Marasmius scorodonius

<400> SEQUENCE: 16

Arg Gly Leu Ala Phe Val Ala Tyr Gln Ser Asn Ile
1               5                   10

<210> SEQ ID NO 17
<211> LENGTH: 19
<212> TYPE: PRT
<213> ORGANISM: Marasmius scorodonius

<400> SEQUENCE: 17

Asp Phe Val Val Ser Arg Gly Gly Glu Tyr Phe Phe Ser Pro Ser Leu
1               5                   10                  15

Ser Ala Ile
```